United States Patent [19]

Kaneko et al.

[11] Patent Number: 4,599,337
[45] Date of Patent: Jul. 8, 1986

[54] ANTIPHLOGISTIC/ANTIPYRETIC-/ANALGESIC AGENTS CONTAINING THEOBROMINE OR THEOPHYLLINE DERIVATIVES AS ACTIVE INGREDIENT

[75] Inventors: Takeru Kaneko, Saitama; Satoru Ozaki, Hoya; Kimie Takizawa, Narashino; Hachiro Sugimoto, Ushiku, all of Japan

[73] Assignee: Eisai Co., Ltd., Tokyo, Japan

[21] Appl. No.: 755,404

[22] Filed: Jul. 16, 1985

Related U.S. Application Data

[62] Division of Ser. No. 471,564, Mar. 2, 1983, Pat. No. 4,543,253.

[51] Int. Cl.$^4$ ............................................. A61K 31/52
[52] U.S. Cl. ..................................... 514/265; 514/263
[58] Field of Search ................................. 514/265, 263

[56] References Cited

U.S. PATENT DOCUMENTS 4,073,908  2/1978  Quelet .................................. 514/265
4,275,064  6/1984  Bodor et al. ......................... 514/265

Primary Examiner—Stanley J. Friedman
Attorney, Agent, or Firm—Flynn, Thiel, Boutell & Tanis

[57] ABSTRACT

Treatment methods are disclosed which utilize antiphlogistic/antipyretic/analgesic agents containing as active ingredient theobromine and theophylline derivatives represented by the general formula:

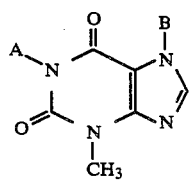

wherein one of A and B is —CH$_3$ and the other of A and B is

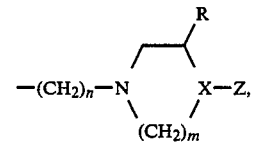

wherein R is a hydrogen atom or a lower alkyl group, Z is selected from the group consisting of (1) a group of the formula

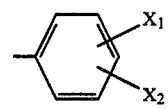

wherein X$_1$ and X$_2$ are the same or different and each represents a hydrogen atom, a lower alkyl group, a lower alkoxy group, a trifluoromethyl group or a halogen atom; (2) a pyridyl group; or (3) a group of the formula:

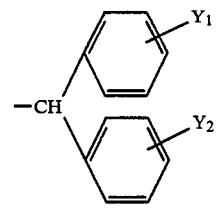

wherein Y$_1$ and Y$_2$ may be the same or different and Y$_1$ and Y$_2$ are selected from the group consisting of a hydrogen atom, a lower alkyl group, a lower alkoxy group, a trifluoromethyl group and a halogen atom, X is a nitrogen atom or a carbon atom, m is 2 or 3, and n is an integer of from 2 to 10, with the provisos that when (i) A is —CH$_3$, m is 2, and (ii) when A is

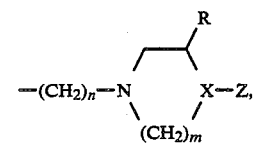

Z is not pyridyl and X is nitrogen, and acid addition salts thereof.

12 Claims, No Drawings

ANTIPHLOGISTIC/ANTIPYRETIC/ANALGESIC AGENTS CONTAINING THEOBROMINE OR THEOPHYLLINE DERIVATIVES AS ACTIVE INGREDIENT

This is a division of application Ser. No. 471 564, filed Mar. 2, 1983, now U.S. Pat. No. 4,543,253.

This invention relates to antiphlogistic/antipyretic-/analgesic agents containing theobromine or theophylline derivatives as the active ingredient thereof. More specifically, the invention relates to treatment methods which utilize antiphlogistic/antipyretic/analgesic agents containing as active ingredients theobromine and theophylline derivatives of the general formula:

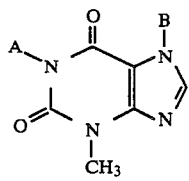

wherein one of A and B is —CH$_3$ and the other of A and B is

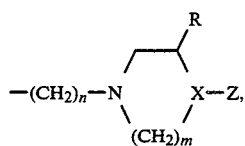

wherein R is a hydrogen atom or a lower alkyl group, Z is selected from the group consisting of (1) a group of the formula

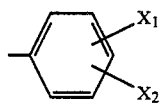

wherein X$_1$ and X$_2$ are the same or different and each represents a hydrogen atom, a lower alkyl group, a lower alkoxy group, a trifluoromethyl group or a halogen atom; (2) a pyridyl group; and (3) a group of the formula:

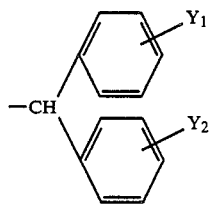

wherein Y$_1$ and Y$_2$ are the same or different and Y$_1$ and Y$_2$ are selected from the group consisting of a hydrogen atom, a lower alkyl group, a lower alkoxy group, a trifluoromethyl group and a halogen atom, X is a nitrogen atom or a carbon atom, m is 2 or 3, and n is an integer of from 2 to 10, with the provisos that (i) when A is —CH$_3$, m is 2, and (ii) when A is

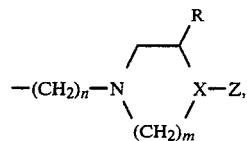

Z is not pyridyl and X is nitrogen, and acid addition salts thereof. More particularly, preferred compounds used in this invention have the following general formulas:

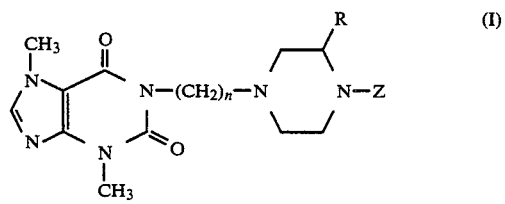

wherein R is a hydrogen atom or a lower alkyl group, Z is a group represented by the formula:

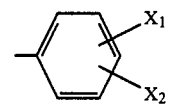

wherein X$_1$ and X$_2$ can be the same or different and each represents a hydrogen atom, a lower alkyl group, a lower alkoxy group, a trifluoromethyl group or a halogen atom, or a group represented by the formula:

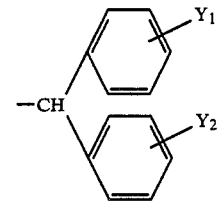

wherein Y$_1$ and Y$_2$ can be the same or different and each represents a hydrogen atom, a lower alkyl group, a lower alkoxy group, a trifluoromethyl group or a halogen atom, and n is an integer of 2 to 10, and acid addition salts thereof, and

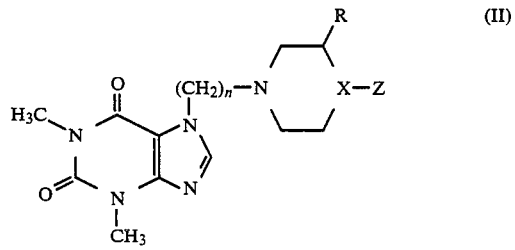

wherein R is a hydrogen atom or a lower alkyl group, Z is a group represented by the formula:

wherein $X_1$ and $X_2$ can be the same or different and each represents a hydrogen atom, a lower alkyl group, a lower alkoxy group, a trifluoromethyl group or a halogen atom, a pyridyl group or a group represented by the formula:

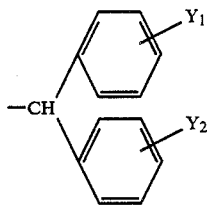

wherein $Y_1$ and $Y_2$ can be the same or different and each represents a hydrogen atom, a lower alkyl group, a lower alkoxy group, a trifluoromethyl group or a halogen atom, X is a nitrogen or carbon atom, and n is an integer of 2 to 10, and acid addition salts thereof.

The lower alkyl groups and lower alkoxy groups in the above definitions of R, $X_1$, $X_2$, $Y_1$ and $Y_2$ in the general formulas (I) and (II) are straight-chain or branched alkyl groups having 1 to 6 carbon atoms, such as methyl, ethyl, n-propyl, isopropyl, n-butyl, isobutyl, 1-methylpropyl, tert-butyl, n-pentyl, 1-ethylpropyl, isoamyl, n-hexyl or the like, and the corresponding alkoxy groups. The halogen atoms in the above definitions are chlorine, bromine, iodine or fluorine atoms.

The compounds (I) and (II) of this invention can be easily converted into acid addition salts by reacting said compounds with a pharmacologically acceptable inorganic or organic acid. Examples of inorganic acids usable for this purpose are hydrochloric acid, hydrobromic acid, hydriodic acid, sulfuric acid and the like. Examples or organic acids usable for this purpose are maleic acid, fumaric acid, succinic acid, acetic acid, malonic acid, citric acid, benzoic acid and the like.

Typical examples of compounds of formula (II), which are theophylline compounds of this invention, are listed below, but of course the present invention is not limited to the use of these compounds.

7-(2-(4-p-chlorobenzhydrylpiperazinyl-(1))-ethyl)-theophylline
7-(3-(4-p-chlorobenzhydrylpiperazinyl-(1))-n-propyl)-theophylline
7-(4-(4-p-chlorobenzhydrylpiperazinyl)-(1))-n-butyl)-theophylline
7-(5-(4-p-methylbenzhydrylpiperazinyl-(1))-n-pentyl)-theophylline
7-(6-(4-p-methoxybenzhydrylpiperazinyl-(1))-n-hexyl)-theophylline
7-(7-(4-o-trifluoromethylbenzhydrylpiperazinyl-(1))-n-heptyl)theophylline
7-(8-(4-benzhydrylpiperazinyl)-(1))-n-octyl)theophylline
7-(9-(4-p-chlorobenzhydrylpiperazinyl-(1))-n-nonyl)-theophylline
7-(10-(4-p-ethoxybenzhydrylpiperazinyl-(1))-n-decyl)-theophylline
7-(4-(4-(4',4''-dichlorodiphenylmethyl)piperazinyl-(1))-n-butyl)theophylline
7-(2-((4-phenyl)piperazinyl-(1))ethyl)theophylline
7-(3-((4-phenyl)piperazinyl-(1))-n-propyl)theophylline
7-(4-((4-phenyl)piperazinyl-(1))-n-butyl)theophylline
7-(5-((4-phenyl)piperazinyl)-(1))-n-pentyl)theophylline
7-(6-((4-phenyl)piperazinyl-(1))-n-hexyl)theophylline
7-(2-(4-o-methylphenylpiperazinyl(1))ethyl)theophylline
7-(3-(4-o-methylphenylpiperazinyl-(1))-n-propyl)theophylline
7-(5-(4-o-methylphenylpiperazinyl-(1))-n-pentyl)theophylline
7-(2-(4-m-methylphenylpiperazinyl-(1))ethyltheophylline
7-(4-(4-m-methylphenylpiperazinyl-(1))-n-butyl)theophylline
7-(5-(4-m-methylphenylpiperazinyl-(1))-n-pentyl)theophylline
7-(6-(4-m-methylphenylpiperazinyl-(1))-n-hexyl)theophylline
7-(2-(4-(2,3-dimethylphenyl)piperazinyl-(1))ethyl)-theophylline
7-(2-(4-(2,6-dimethylphenyl)piperazinyl)-(1))ethyl)-theophylline
7-(3-(4-b 2,6-dimethylphenyl)piperazinyl-(1))-n-propyl)theophylline
7-(4-(4-(2,6-dimethylphenyl)piperazinyl-(1))-n-butyl)-theophylline
7-(5-(4-(2,6-dimethylphenyl)piperazinyl-(1))-n-pentyl)-theophylline
7-(6-(4-(2,6-dimethylphenyl)piperazinyl-(1))-n-hexyl)-theophylline
7-(3-(4-(2,3-dimethylphenyl)piperazinyl-(1))-n-propyl)-theophylline
7-(4-(4-(2,3-dimethylphenyl)piperazinyl-(1))-n-butyl)-theophylline
7-(5-(4-(2,3-dimethylphenyl)piperazinyl)-(1))-n-pentyl)-theophylline
7-(6-(4-(2,3-dimethylphenyl)piperazinyl-(1))-n-hexyl)-theophylline
7-(2-(4-(2,5-dimethylphenyl)piperazinyl)-(1))ethyl)-theophylline
7-(3-(4-(2,5-dimethylphenyl)piperazinyl-(1))-n-propyl)-theophylline
7-(4-(4-(2,5-dimethylphenyl)piperazinyl-(1))-n-butyl)-theophylline
7-(5-(4-(2,5-dimethylphenyl)piperazinyl-(1))-n-pentyl)-theophylline
7-(6-(4-(2,5-dimethylphenyl)piperazinyl-(1))-n-hexyl)-theophylline
7-(2-(4-o-methoxyphenylpiperazinyl-(1))ethyl)theophylline
7-(3-(4-o-methoxyphenylpiperazinyl-(1))-n-propyl)-theophylline
7-(4-(4-o-methoxyphenylpiperazinyl-(1))-n-butyl)theophylline
7-(5-(4-o-methoxyphenylpiperazinyl-(1))-n-pentyl)-theophylline
7-(6-(4-o-methoxyphenylpiperazinyl-(1))-n-hexyl)-theophylline 7-(2-(4-m-methoxyhenylpiperazinyl-(1))ethyl)theophylline
7-(3-(4-m-methoxyphenylpiperazinyl-(1))-n-propyl)theophylline
7-(4-(4-m-methoxyphenylpiperazinyl-(1))-n-butyl)theophylline
7-(5-(4-m-methoxyphenylpiperazinyl-(1))-n-pentyl)theophylline
7-(6-(4-m-methoxyphenylpiperazinyl-(1))-n-hexyl)theophylline
7-(2-(4-p-methoxyphenylpiperazinyl-(1))-ethyl)theophylline
7-(4-(4-p-methoxyphenylpiperazinyl-(1))-n-butyl)theophylline
7-(5-(4-p-methoxyphenylpiperazinyl-(1))-n-pentyl)theophylline
7-(6-(4-p-methoxyphenylpiperazinyl-(1))-n-hexyl)theophylline
7-(2-(4-o-chlorophenylpiperazinyl-(1))ethyl)theophylline
7-(4-(4-o-chlorophenylpiperazinyl-(1))-n-butyl)theophylline
7-(5-(4-o-chlorophenylpiperazinyl-(1))-n-pentyl)theophylline
7-(6-(4-o-chlorophenylpiperazinyl-(1))-n-hexyl)theophylline
7-(2-(4-m-chlorophenylpiperazinyl-(1))ethyl)theophylline
7-(4-(4-m-chlorophenylpiperazinyl-(1))-n-butyl)theophylline
7-(5-(4-m-chlorophenylpiperazinyl-(1))-n-pentyl)theophylline
7-(2-(4-o-chlorophenylpiperazinyl-(1))-ethyl)theophylline
7-(4-(4-o-chlorophenylpiperazinyl-(1))-n-butyl)theophylline
7-(5-(4-o-chlorophenylpiperazinyl-(1))-n-pentyl)theophylline
7-(6-(4-o-chlorophenylpiperazinyl-(1))-n-hexyl)theophylline
7-(2-(4-(3,4-dichlorophenyl)piperazinyl-(1))ethyl)theophylline
7-(3-(4-(3,4-dichlorophenyl)piperazinyl-(1))-n-propyl)theophylline
7-(4-(4-(3,4-dichlorophenyl)piperazinyl-(1))-n-butyl)theophylline
7-(3-(4-p-fluorophenylpiperazinyl-(1))-n-propyl)theophylline
7-(4-(4-p-fluorophenylpiperazinyl)-(1))-n-butyl)theophylline
7-(3-(4-m-trifluoromethylphenylpiperazinyl-(1))-n-propyl)theophylline
7-(4-(4-m-trifluoromethylphenylpiperazinyl-(1))-n-butyl)theophylline
7-(5-(4-m-trifluoromethylphenylpiperazinyl-(1))-n-pentyl)theophylline
7-(4-(4-o-trifluoromethylphenylpiperazinyl-(1))-n-butyl)theophylline
7-(3-(4-p-trifluoromethylphenylpiperazinyl-(1))-n-propyl)theophylline
7-(2-(4-(2-pyridyl)piperazinyl-(1))ethyl)theophylline
7-(3-(4-(2-pyridyl)piperazinyl-(1))-n-propyl)theophylline
7-(4-(4-(2-pyridyl)piperazinyl-(1))-n-butyl)theophylline
7-(5-(4-(2-pyridyl)piperazinyl-(1))-n-pentyl)theophylline
7-(6-(4-(2-pyridyl)piperazinyl-(1))-n-hexyl)theophylline
7-(7-((3-methyl-4-m-methylphenyl)piperazinyl-(1))-n-heptyl)theophylline
7-(2-((3-methyl-4phenyl)piperazinyl-(1))ethyl)theophylline
7-(4-((3-methyl-4-phenyl)piperazinyl-(1))-n-butyl)theophylline
7-(5-((3-methyl-4-phenyl)piperazinyl-(1))-n-pentyl)theophylline
7-(2-((3-methyl-4-p-methoxyphenyl)piperazinyl-(1))-ethyl)theophylline
7-(5-((3-methyl-4-p-methoxyphenyl)piperazinyl-(1))-n-pentyl)theophylline
7-(6-((3-ethyl-4-p-methoxyphenyl)piperazinyl-(1))-n-hexyl)theophylline
7-(7-(4-m-chlorophenylpiperazinyl-(1))-n-heptyl)theophylline
7-(8-(4-(3,4-dimethylphenyl)piperazinyl-(1))-n-octyl)theophylline
7-(9-(4-(2,3-diethylphenyl)piperazinyl-(1))-n-nonyl)theophylline
7-(10-(4-m-ethoxyphenylpiperazinyl)-(1))-n-decyl)theophylline
7-(7-(4-(2,3-dimethylphenyl)piperazinyl-(1))-n-heptyl)theophylline
7-(7-(4-(2-methyl-3-ethylphenyl)piperazinyl-(1))-n-heptyl)theophylline
7-(3-(4-(2-methyl-3-n-propylphenyl)piperazinyl-(1))-n-propyl)theophylline
7-(2-((4-phenyl)piperidinyl)ethyl)theophylline
7-(3-((4-phenyl)piperidinyl)-n-propyl)theophylline
7-(4-((4-phenyl)piperidinyl)-n-butyl)theophylline
7-(5-((4-p-chlorophenyl)piperidinyl)-n-pentyl)theophylline
7-(5-(4-(3,4-dichlorophenyl)piperazinyl-(1))-n-pentyl)theophylline
7-(7-(4-(2-methyl-5-chlorophenyl)piperazinyl-(1))-n-heptyl)theophylline
7-(10-((4-o-methoxyphenyl)piperazinyl-(1))-n-decyl)theophylline
7-(10-(4-(2-methyl-5-chlorophenyl)piperazinyl-(1))-n-decyl)theophylline
7-(10-(3-methyl-4-m-methylphenylpipeazinyl-(1))-n-decyl)theophylline
7-(10-(4-3,4-dimethylphenyl)piperazinyl-(1))-n-decyl)theophylline The present inventors have carried out studies on said theobromine and theophylline derivatives of formulas (I) and (II) as pharmaceuticals and unexpectedly found that said derivatives have excellent analgesic, antipyretic and antiphlogistic activities, and the present invention was attained on the basis of these findings. The theobromine and theophylline derivatives used in the treatment methods of this invention are strikingly different in chemical structure from conventional antipyretic/analgesic or antiphlogistic agents.

The compounds of formula (I) of this invention, which are theobromine compounds, can be prepared by various processes, of which one typical example may be expressed as follows:

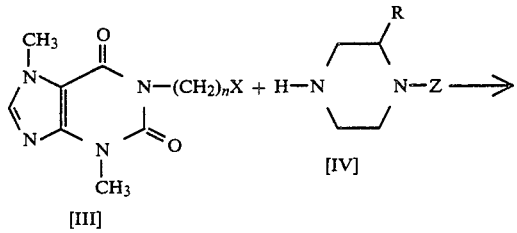

wherein X is a halogen atom or a p-toluene-sulfonyloxy group, and R and n are the same as defined above. Thus, essentially, the compounds of formula (I) of this invention can be obtained by reacting compounds of the general formula (III) with those of the general formula (IV).

The compounds of formula (II) of this invention, which are theophylline compounds, can be prepared by various processes, of which one typical example may be expressed as follows:

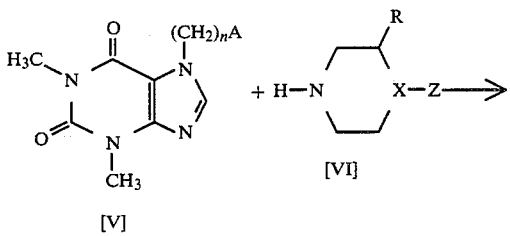

wherein A is a halogen atom or a p-toluene-sulfonyloxy group, and R, X, Z and n are as defined above.

Thus, the compounds of formula (II) of this invention can be obtained by reacting compounds of formula (V) with those of formula (VI).

The foregoing reactions used to produce the compounds of formulas (I) and (II) of this invention can be performed in the absence of a solvent, or in the presence of a suitable solvent selected from lower alcohols such as methanol, ethanol, propanol, or isopropanol, aromatic solvents such as benzene, toluene, or xylene, or ethers such as diethyl ether or tetrahydrofuran, which take no part in the reaction. Although the reaction can proceed at room temperature, it is desirable to heat the reaction system to the boiling point of the solvent used. Addition of an acid trapping agent, such as triethylamine, an alkali bicarbonate, an alkali carbonate, or pyridine to the reaction system allows the reaction to be conducted with enhanced smoothness.

The pharmacological effects and toxicities of the compounds of this invention will be shown below by reference to test examples.

TEST EXAMPLE

1. Test method (1) Analgesic activity (a) Acetic acid writhing method[1]

A 0.7% acetic acid solution was injected intraperitoneally to ddy-strain male mice (20 to 25 g) in an amount of 0.1 ml per 10 g mouse body weight to cause a writhing syndrome typified by stretching of the hind legs. The inhibitory action of each test compound against said symptom was observed as a measure of the analgesic activity of the compound. In the tests, each of the compounds of this invention and each of the control drugs listed below were administered orally to each test animal, and 50 minutes later said acetic acid solution was injected in the manner described above and the total number of typical writhes was determined over a period of 15 minutes. The Litchfield-Wilcoxon's method (See note 2) was used for determining the 50% effective dose ($ED_{50}$).

Notes: (1) Hendershot, L. C. and Forsaith, J.: J. Pharmacol. Exp. Ther., 125, 237 (1959).
(2) Litchfield, Jr., J. T. and Wilcoxon, F.: J. Pharmacol. Exp. Ther., 96, 99 (1949).

(b) Bradykinin-induced pain response[3,4]

A polyethylene tube was inserted into a common right carotid artery of SD male rats (250 to 350 g) and 0.5 microngram per 0.1 ml of bradykinin was injected into the artery through said tube. Response induced by bradykinin such as flexin of the right forelimb, dextrorotation of the head and rearing were considered as being indices of pain response, and the analgesic action of each test compound was determined by observing its inhibition of responses such symptoms.

Notes: (3) T. Abe, T. Kaneko and H. Takagi: Japan Pharm. Soc. Bul., 67, 9–14 (1971)
(4) G. F. Blane: J. Pharma. Pharmacol., 19, 367 (1967)

(2) Antipyretic activity

A 2% suspension of dry yeast was injected subcutaneously to SD male rats of 250 to 300 g body weight in an amount of 2 ml/animal to cause a fever, and 4 hours later, the compounds of this invention and control drugs were administered orally. The rectal temperature of each rat was measured periodically, and the dosage of each compound required to reduce the fever by more than 1° C. at the peak of its activity was determined.

(3) Antiphlogistic activity[5]

Each test compound of this invention was administered orally to Wistar rats of about 300 g body weight, and 30 minutes later 0.05 ml of a 1% carrageenin solution was injected into a paw of each rat. After three hours, the paw volume was measured to determine the degree of edema formation and the 30% effective dose ($ED_{30}$) was calculated from the inhibition rate relative to a control group.

Note: (5) R. Vinegar et al: J. Pharmacol. Exp. Ther., 166, 96 (1969)

(4) Acute toxicity

The acute toxicity of the compounds of the invention was examined using ddy male mice and SD male rats, and the 50% lethal dose ($LD_{50}$) was determined. Ten mice were used for each dose and morality was determined for 3 days after administration of each test compound of the invention. In the case of the rats, 5 rats were used for each dose and morality was determined 7 days after administrations.

2A. Test compounds of formula (II)

Compound A: 7-(4-(4-p-fluorophenylpiperazinyl-(1))-n-butyl)theophylline.2HCl

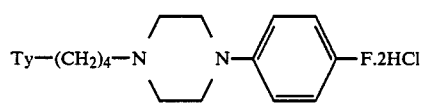

Compound B: 7-(5-(4-p-chlorophenylpiperazinyl-(10))-n-pentyl)theophylline.2HCl

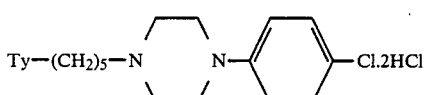

Compound C: 7-(3-(4-(3,4-dimethylphenyl)piperazinyl-(1))-n-propyl)theophylline.2HCl

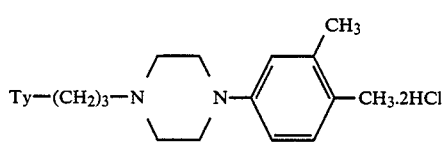

Compound D: 7-(4-(4-p-chlorophenylpiperazinyl-(1))-n-butyl)theophylline.2HCl

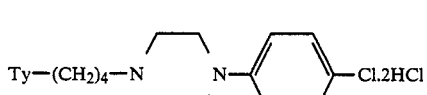

Compound E: 7-(4-(4-(2,3-dimethylphenyl)piperazinyl-(1))-n-butyl)theophylline.2HCl

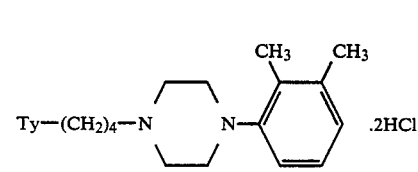

Compound F: 7-(5-(4-m-trifluoromethylphenylpiperazinyl-(1))-n-pentyl)theophylline.2HCl

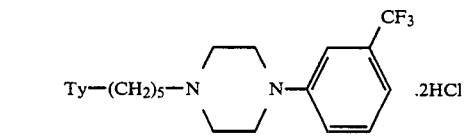

In the above structural formulae, Ty stands for

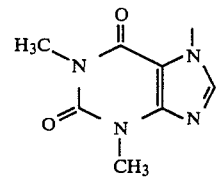

Control drug I: Mepirizole (4-methoxy-2-(5-methoxy-3-methylpyrazol-1-yl)-6-methylpyrimidine)

Control drug II: Thiaramide (4-((5-chloro-2-oxo-3(2H)-benzothiazolyl)acetyl)-1-piperazineethanol)

Control drug III: Perisoxal (3-(1-hydroxy-2-piperadino-ethyl)-5-phenyl-isoxazole)

2B. Test compounds of Formula (I)

Compound A': 1-(3-(4-(3,4-dichlorophenyl)piperazinyl-(1))-n-propyl)theobromine

Compound B': 1-(2-(4-(2,3-dimethylphenyl)piperazinyl-(1))-ethyl)theobromine.2HCl Compound C': 1-(3-(4-o-chlorophenylpiperazinyl-(1))-n-propyl)theobromine.2HCl Compound D': 1-(4-(4-o-methoxyphenylpiperazinyl-(1))-n-butyl)theobromine.2HCl

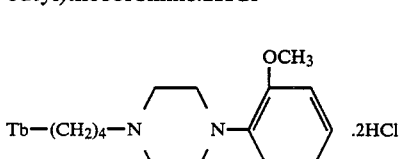

Compound E': 1-(4-(4-p-fluoropenylpiperazinyl-(1))-n-butyl)theobromine.2HCl

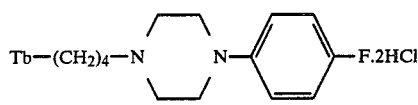

Compound F': 1-(4-(4-(3,4-dichlorophenyl)piperazinyl-(1))-n-butyl)theobromine.2HCl

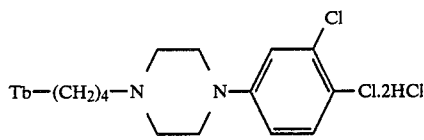

Compound G': 1-(5-(4-m-methylphenylpiperazinyl-(1))-n-pentyl)theobromine.2HCl

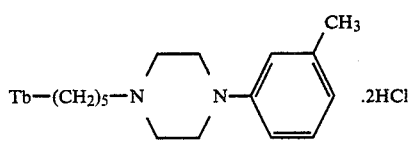

In the above structural formulae, Tb stands for the following formula:

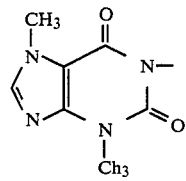

3. Results (1) Analgesic activity and acute toxicity

The analgesic activity ($ED_{50}$), 50% lethal dose ($LD_{50}$) and safety margin ($LD_{50}/ED_{50}$) as determined in the tests on the mice for compounds A to F are shown in Table 1.

It is clear from Table 1 that the compounds of formula (II) used in this invention, as compared with the control drugs, have a strong analgesic activity (2.5 to 24 times that of the control drugs) and also have a wide safety margin.

Table 2 shows the analgesic activity ($ED_{50}$), 50% lethal dose ($LD_{50}$) and safety margin ($LD_{50}/ED_{50}$) as determined in the tests on the rats for compounds A to F.

It is apparent from Table 2 that the compounds of formula (II) of this invention, as compared with the control drugs, have a strong analgesic activity more than 3 times that of the control drugs.

TABLE 1

| Test compounds | Analgesic activity $ED_{50}$ mg/kg p.o. | Acute toxicity $LD_{50}$ mg/kg p.o. | Safety margin ($LD_{50}/ED_{50}$) |
| --- | --- | --- | --- |
| Compound A | 10 | 344 | 34 |
| Compound B | 13.8 | 704 | 51 |
| Compound C | 13.3 | 800≦ | 60< |
| Compound D | 26.0 | 575 | 22 |
| Compound F | 14.5 | 408 | 28 |
| Compound F | 27.1 | 800≦ | 30≦ |

TABLE 1-continued

| Test compounds | Analgesic activity $ED_{50}$ mg/kg p.o. | Acute toxicity $LD_{50}$ mg/kg p.o. | Safety margin ($LD_{50}/ED_{50}$) |
| --- | --- | --- | --- |
| Control drug I | 240 | 1,022* | 4.3 |
| Control drug II | 66 | 664* | 8.5 |
| Control drug III | 120 | 612* | 5.1 |

Note
*$LD_{50}$'s of control drugs I, II and III are those given in Japan National Formulary, 6th Ed. (1982).

TABLE 2

| Test compounds | Analgesic activity $ED_{50}$ mg/kg p.o. | Acute toxicity $LD_{50}$ mg/kg p.o. | Safety margin ($LD_{50}/ED_{50}$) |
| --- | --- | --- | --- |
| Compound A | 47 | 353–500 | 7.5–10.6 |
| Compound B | 40 | 353–500 | 8.8–12.5 |
| Compound C | 57 | 770 | 13.6 |
| Compound D | 68 | 505 | 7.6 |
| Compound E | 66 | 353–500 | 7.6–5.3 |
| Compound F | 63 | 660 | 10.5 |
| Control drug I | 160≦ | 526* | 3≧ |
| Control drug II | 160≦ | 3,600* | 23≧ |
| Control drug III | 160 | 1,978* | 12 |

Note
*$LD_{50}$'s of the control drug I, II and III are those given in Japan National Formulary, 6th Ed. (1982).

The analgesic activity ($ED_{50}$), 50% lethal dose ($LD_{50}$) and safety margin ($LD_{50}/ED_{50}$) as determined in the tests on the mice for compounds A' to G' are shown in Table 3.

It is clear from Table 3 that the compounds of formula (I) used in this invention, as compared with the control drugs, also have a strong analgesic activity (2 to 90 times that of the control drugs) and have a wide safety margin.

Table 4 shows the analgesic activity ($ED_{50}$), 50% lethal dose ($LD_{50}$) and safety region ($LD_{50}/ED_{50}$) as determined in the tests on the rats for compounds A'-G'.

It is apparent from Table 4 that the theobromine compounds for formula (I) of this invention, as compared with the control drugs, have a strong analgesic activity which is 4 to 8 times that of the control drugs. As a further unexpected result, it was observed that the theobromine compounds of formula (I) were several times more potent in their analgesic effects than the theophylline compounds of formula (II). For analgesic treatments according to this invention, it is therefore particularly preferred to use compounds of the formula (I), wherein R is a hydrogen atom and Z is

with the proviso that at least one of $X_1$ and $X_2$ is not hydrogen.

TABLE 3

| Test compounds | Analgesic activity $ED_{50}$ mg/kg p.o. | Acute toxicity $LD_{50}$ mg/kg p.o. | Safety margin ($LD_{50}/ED_{50}$) |
| --- | --- | --- | --- |
| Compound A' | 7.2 | 800< | φ> |
| Compound B' | 2.6 | 600 | 230 |
| Compound C' | 3.3 | 200 | 61 |

TABLE 3-continued

| Test compounds | Analgesic activity ED$_{50}$ mg/kg p.o. | Acute toxicity LD$_{50}$ mg/kg p.o. | Safety margin (LD$_{50}$/ED$_{50}$) |
| --- | --- | --- | --- |
| Compound D' | 3.1 | 400–800 | 130–258 |
| Compound E' | 7.8 | 200 | 26 |
| Compound F' | 7.8 | 400–800 | 51–103 |
| Compound G' | 13.5 | 300 | 22 |
| Control drug I | 240 | 1022* | 4.3 |
| Control drug II | 66 | 564* | 8.5 |
| Control drug III | 120 | 612* | 5.1 |

Note
*LD$_{50}$'s of control drugs I, II and III are those given Japan National Formulary, 6th Ed. (1982).

TABLE 4

| Test compounds | Analgesic activity ED$_{50}$ mg/kg p.o. | Acute toxicity LD$_{50}$ mg/kg p.o. | Saftety margin (LD$_{50}$/ED$_{50}$) |
| --- | --- | --- | --- |
| Compound A' | 40 | 2,000≦ | 50≦ |
| Compound B' | 20 | 2,000≦ | 100≦ |
| Control drug I | 160≦ | 526* | 3≧ |
| Control drug II | 160≦ | 3,600* | 23≧ |
| Control drug III | 160 | 1,978* | 12 |

Note
*LD$_{50}$'s of control drug I, II and III are those given in Japan National Formulary, 6th, Ed. (1982).

2. Antipyretic activity

The results for the test compounds of formula (II) are given in Table 5.

For compounds A to F, Table 5 shows that the compounds of formula (II) used in this invention showed an antipyretic activity at a dosage of from 10 to 40 mg/kg p.o. and are equal to or about 4 times as strong as the control drugs in antipyretic action.

TABLE 5

| Test compounds | ED* mg/kg p.o. |
| --- | --- |
| Compound A | 10 |
| Compound B | 40 |
| Compound C | 10 |
| Compound D | 40 |
| Compound E | 40 |
| Compound F | 10 |
| Control drug I | 40 |
| Control drug II | 40 |
| Control drug III | 160 |

Note
*Effective dose for reducing the fever by more than 1° C. when the compound action is at the peak.

The results of examinations on Compound A', a typical compound of formula (I) of this invention, were that its effective dose ED* (mg/kg p.o.) for reducing the fever by more than 1° C. at the peak of its activity was 40 mg/kg p.o. Comparing this with the similarly-determined ED values for the control drugs, 40 mg/kg p.o. for control drug I, 40 mg/kg p.o. for control drug II and 160 mg/kg p.o. for control drug III, it is noted that the antipyretic activity of Compound A' is equal to or about 4 times greater than the antipyretic activities of the control drugs.

As to the method of treating a fever according to the present invention, compounds of the formulas (I) and (II) wherein R is a hydrogen atom and Z is

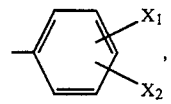

with the proviso that one of $X_1$ and $X_2$ is not hydrogen, are particularly preferred.

(3) Antiphlogistic activity

The results are given in Tables 6 and 7.

As seen from Table 6, the compounds of formula (II) of this invention showed an antiphlogistic activity at doses of from 10 to 50 mg/kg.

TABLE 6

| Test compounds | ED$_{30}$ mg/kg p.o. |
| --- | --- |
| Compound A | 10 |
| Compound B | 50 |
| Compound D | 25 |
| Compound E | 25 |
| Compound F | 25 |

Table 7 shows that the compounds of formula (I) of this invention which were tested showed an antiphlogistic activity at doses of from 10 to 25 mg/kg. The foregoing dosage range is preferred but not critical to the method of treating inflammation and swelling of tissues according to the present invention.

TABLE 7

| Test compounds | ED$_{30}$ mg/kg p.o. |
| --- | --- |
| Compound A' | 25 |
| Compound C' | 10 |
| Compound E' | 25 |
| Compound G' | 25 |

Compounds of the formulas (I) and (II) wherein R is hydrogen, Z is

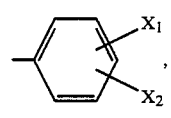

and at least one of $X_1$ and $X_2$ is not hydrogen are preferred for use in the method of treating inflammation and swelling of tissues and/or bones and joints of the present invention.

As is apparent from the foregoing test results, the theophylline and theobromine derivatives used in this invention possess strong analgesic, antipyretic and antiphlogistic activities and are useful as antiphlogistic/antipyretic/analgesic agents, and thus the present invention is of high pharmaceutical value.

The compounds of this invention can be administered either perorally or parenterally, particularly intramuscularly, subcutaneously or intravenously. Effective dosages vary depending on the type of disease, the severity of the symptoms, age of the patient and other factors, but usually it is preferable, though not critical, to administer the compound in dosages of from about 1 to 1,000 mg, more preferably about 3 to 100 mg, per day for adult human beings.

The compounds used in this invention can be incorporated into any suitable pharmaceutical preparations, such as tablets, granules, powders, capsules, injection solutions, or suppositories, by the conventional methods known in the art of drug formulation.

When a peroral solid pharmaceutical is prepared, for instance, the active compound is mixed with an excipient and, if necessary, further mixed with other adjuncts, such as a binder, a disintegrator, a lubricant, a coloring agent, a taste and smell improver and the like, and the resulting mixture is then worked up into a suitable drug unit dosage form, such as a tablet, a coated tablet, granules, a powder, or a capsule in the conventional way.

As the excipient, there can be used, for example, lactose, corn starch, white sugar, dextrose, sorbitol, crystalline cellulose or the like, and as the binder, there can be used polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone or the like. As the disintegrator, there can be used starch, agar-agar, gelatin powder, crystalline cellulose, calcium carbonate, sodium bicarbonate, calcium citrate, dextrin, pectin or the like, and as the lubricant, magnesium stearate, talc, polyethylene glycol, silica, hardened vegetable oils or the like can be used. As for the coloring agent, it is impossible to use any materials suitable for addition to drugs. As the taste and smell improver, there can be used cocoa powder, menthol, aromatic acids, peppermint oil, borneo camphor, cinnamon powder or the like. Tablet and granular preparations can be suitably coated with sugar, gelatin or the like.

For the preparation of injectable solutions, a pH adjuster, a buffer agent, a stabilizer, a preservative and other necessary adjuvants are added to the active ingredient, and the mixture may then be made into a desired type of injection solution, such as solutions for subcutaneous, intramuscular, or intravenous injection in the conventional way.

Synthesis examples of the present invention are given below.

SYNTHESIS EXAMPLE 1

7-(2-(4-p-Chlorobenzhydrylpiperazinyl-(1))ethyl)-theophylline hydrochloride 6.3 g of 7-(2-bromoethyl)theophylline, 5.7 g of 1-(p-chlorobenzhydryl)piperazine and 4.0 g of triethylamine was stirred in benzene under reflux for 18.5 hours. The triethylamine hydrochloride formed was then filtered off and the filtrate was extracted with dilute hydrochloric acid. The extract was made alkaline with dilute sodium hydroxide and then further extracted with chloroform. The chloroform layer was washed with water and dried over anhydrous potassium carbonate. The solvent was distilled off and the resulting crude crystals were converted into the hydrochloride thereof by a conventional method and then recrystallized from methyl cellosolve and water to obtain 4.8 g of the product compound 7-(2-(4-p-chlorobenzhydrylpiperazinyl-(1))ethyl)theophylline hydrochloride (yield: 42.5%).

Melting point: 250°–252° C.

| Elemental analysis for $C_{26}H_{29}O_2N_6.2HCl$: | | | |
|---|---|---|---|
| | C | H | N |
| Calculated (%): | 55.16 | 5.53 | 14.85 |
| Found (%): | 55.19 | 5.38 | 14.87 |

SYNTHESIS EXAMPLE 2

7-(4-(4-o-Methoxyphenylpiperazinyl-(1))-n-butyl)-theophylline 6.9 g of 7-(4-bromo-n-butyl)theophylline, 3.8 g of 1-(o-methoxyphenyl)piperazine and 4.0 g of triethylamine were stirred in benzene under reflux for 18 hours and the mixture was then treated in the same way as in Synthesis Example 1, except that the hydrochloride conversion step was omitted. Recrystallization from ethanol gave 3.8 g of the product compound 7-(4-(4-o-methoxyphenylpiperazinyl-(1))-n-butyl)theophylline (yield: 37.6%).

Melting point: 117°–118° C.

| Elemental analysis for $C_{22}H_{30}O_3N_6$: | | | |
|---|---|---|---|
| | C | H | N |
| Calculated (%): | 61.94 | 7.10 | 19.71 |
| Found (%): | 62.10 | 7.21 | 19.86 |

SYNTHESIS EXAMPLE 3

7-(5-(4-(2,3-Dimethylphenyl)piperazinyl-(1))-n-pentyl)-theophylline 9.9 g of 7-(5-bromo-n-pentyl)theophylline, 3.8 g of 1-(2,3-dimethylphenyl)piperazine and 4.0 g of triethylamine were stirred in toluene under reflux for 11.5 hours and then treated in the same manner as in Synthesis Example 1, except that the hydrochloride conversion step was omitted. Recrystallization from ethanol gave 4.3 g of the desired compound 7-(5-(4-(2,3-dimethylphenyl)piperazinyl-(1))-n-pentyl)theophylline.

Melting point: 115°–117° C.

| Elemental analysis for $C_{24}H_{34}O_2N_6$: | | | |
|---|---|---|---|
| | C | H | N |
| Calculated (%): | 65.71 | 7.38 | 19.16 |
| Found (%): | 65.42 | 7.92 | 19.31 |

SYNTHESIS EXAMPLE 4

7-(7-((3-Methyl-4-(m-methylphenyl))piperazinyl-(1))-n-heptyl)theophylline hydrochloride 7.8 g of 7-(7-bromoheptyl)theophylline, 3.8 g of N-(m-methylphenyl)-2-methylpiperazine and 4.0 g of triethylamine were stirred in toluene under reflux for 11 hours and the mixture was treated in the same manner as in Synthesis Example 1 to obtain 10 g of crude crystals. The crystals were purified by silica gel column chromatography and converted into a hydrochloride thereof by a conventional method to obtain 5.3 g of the desired compound 7-(7-((3-methyl-(4-m-methylphenyl)-)piperazinyl-(1))-n-heptyl)theophylline hydrochloride.
Melting point: 222°–225° C.

| Elemental analysis for $C_{26}H_{38}O_2N_6Cl_2 \cdot \frac{1}{2}H_2O$: | | | |
|---|---|---|---|
| | C | H | N |
| Calculated (%): | 57.02 | 7.38 | 15.35 |
| Found (%): | 57.00 | 7.88 | 15.20 |

SYNTHESIS EXAMPLES 5–95

The compounds shown in Table 8 below were obtained by processes analogous to that of Synthesis Example 1. The compounds below are species according to general formula (II):

TABLE 8

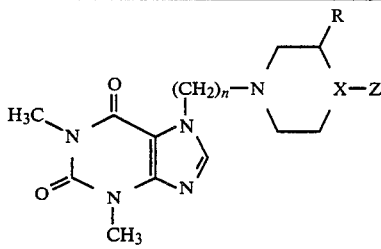

| Synthesis Example No. | n | X | R | Z | Recrystallization solvent | Melting point (°C.) | Molecular formula | Elemental analysis (upper: calculated / lower: found) | | |
|---|---|---|---|---|---|---|---|---|---|---|
| | | | | | | | | C (%) | H (%) | N (%) |
| 5 | 2 | N | H | phenyl | ethanol | 228–234 (decomposed) | $C_{19}H_{24}O_2N_6 \cdot 2HCl$ | 51.70 / 51.53 | 9.45 / 9.16 | 19.04 / 18.70 |
| 6 | 3 | N | H | phenyl | methanol | 143–145 | $C_{20}H_{26}O_2N_6$ | 62.79 / 62.66 | 6.87 / 6.90 | 21.98 / 22.01 |
| 7 | 4 | N | H | phenyl | ethanol | 114–115 | $C_{21}H_{28}O_2N_6$ | 63.60 / 63.61 | 7.13 / 7.25 | 21.20 / 21.34 |
| 8 | 5 | N | H | phenyl | ethanol/isopropyl ether | 112–113 | $C_{22}H_{30}O_2N_6$ | 64.35 / 64.44 | 7.38 / 7.49 | 20.47 / 20.43 |
| 9 | 6 | N | H | phenyl | ethanol/isopropyl ether | 200–203 (decomposed) | $C_{23}H_{32}O_2N_6 \cdot 2HCl$ | 55.52 / 55.26 | 6.90 / 6.71 | 16.90 / 16.59 |
| 10 | 2 | N | H | o-CH$_3$-phenyl | ethanol | 149–150 | $C_{20}H_{26}O_2N_6$ | 62.80 / 62.52 | 6.85 / 6.85 | 21.98 / 21.81 |
| 11 | 3 | N | H | o-CH$_3$-phenyl | ethanol | 114–116 | $C_{21}H_{28}O_2N_6$ | 63.60 / 63.26 | 7.13 / 7.21 | 21.20 / 20.75 |
| 12 | 5 | N | H | o-CH$_3$-phenyl | ethanol/isopropyl ether | 113–114 | $C_{23}H_{32}O_2N_6$ | 65.05 / 65.08 | 7.61 / 7.80 | 19.80 / 19.75 |

TABLE 8-continued

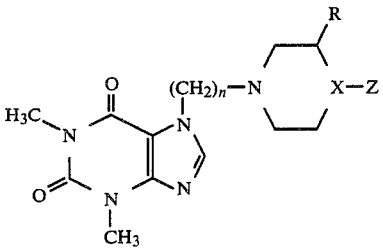

| Synthesis Example No. | n | X | R | Z | Recrystallization solvent | Melting point (°C.) | Molecular formula | Elemental analysis (upper value: calculated / lower value: found) | | |
|---|---|---|---|---|---|---|---|---|---|---|
| | | | | | | | | C (%) | H (%) | N (%) |
| 13 | 2 | N | H | 3-CH₃-C₆H₄ | ethanol | 121–122 | C₂₀H₂₆O₂N₆ | 62.80 / 62.98 | 6.85 / 6.83 | 21.98 / 21.97 |
| 14 | 4 | N | H | 3-CH₃-C₆H₄ | ethanol | 237–239 (decomposed) | C₂₂H₃₀O₂N₆ · 2HCl | 54.66 / 54.57 | 6.67 / 6.69 | 17.39 / 17.47 |
| 15 | 5 | N | H | 3-CH₃-C₆H₄ | methanol | 239–241 (decomposed) | C₂₃H₃₂O₂N₆ · 2HCl | 55.30 / 55.32 | 6.87 / 6.90 | 16.83 / 16.98 |
| 16 | 6 | N | H | 3-CH₃-C₆H₄ | methanol | 224–226 (decomposed) | C₂₄H₃₄O₂N₆ · 2HCl | 56.35 / 56.05 | 7.09 / 7.10 | 16.43 / 16.42 |
| 17 | 2 | N | H | 2,4-(CH₃)₂-C₆H₃ | ethanol/isopropyl ether | 103–106 | C₂₁H₂₈O₂N₆ | 63.61 / 63.64 | 7.12 / 7.03 | 21.20 / 21.05 |
| 18 | 3 | N | H | 2,4-(CH₃)₂-C₆H₃ | ethanol | 116–118 | C₂₂H₃₀O₂N₆ | 64.35 / 64.31 | 7.38 / 7.48 | 20.47 / 20.52 |
| 19 | 4 | N | H | 2,4-(CH₃)₂-C₆H₃ | ethanol | 275–276 (decomposed) | C₂₃H₃₂N₆O₂ · HCl | 59.92 / 59.54 | 7.21 / 7.26 | 18.23 / 18.05 |

TABLE 8-continued

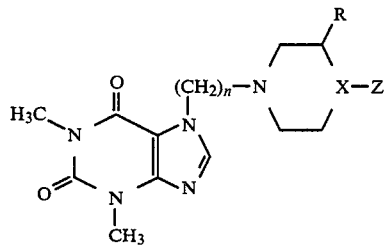

| Synthesis Example No. | n | X | R | Z | Recrystallization solvent | Melting point (°C.) | Molecular formula | Elemental analysis (upper value: calculated / lower value: found) | | |
|---|---|---|---|---|---|---|---|---|---|---|
| | | | | | | | | C (%) | H (%) | N (%) |
| 20 | 5 | N | H | 2,3-(CH₃)₂-C₆H₃ | ethanol | 136–138 | $C_{24}H_{34}O_2N_6$ | 65.71 / 66.00 | 7.83 / 7.94 | 19.16 / 19.13 |
| 21 | 6 | N | H | 2,3-(CH₃)₂-C₆H₃ | ethanol/iso-propyl ether | 167–170 (decomposed) | $C_{25}H_{36}O_2N_6 \cdot 2HCl$ | 57.14 / 56.75 | 7.30 / 7.50 | 15.99 / 16.44 |
| 22 | 2 | N | H | 2,6-(CH₃)₂-C₆H₃ | ethanol | 151–152 | $C_{21}H_{28}O_2N_6$ | 63.61 / 63.93 | 7.12 / 7.17 | 21.20 / 21.26 |
| 23 | 3 | N | H | 2,6-(CH₃)₂-C₆H₃ | methanol | 153–155 | $C_{22}H_{30}O_2N_6$ | 64.36 / 64.08 | 7.38 / 7.46 | 20.48 / 20.10 |
| 24 | 4 | N | H | 2,6-(CH₃)₂-C₆H₃ | ethanol | 114–116 | $C_{23}H_{32}O_2N_6$ | 65.05 / 64.63 | 7.61 / 7.53 | 19.80 / 19.79 |
| 25 | 5 | N | H | 2,6-(CH₃)₂-C₆H₃ | ethanol | 115–117 | $C_{24}H_{34}O_2N_6$ | 65.71 / 65.42 | 7.38 / 7.97 | 19.16 / 19.31 |
| 26 | 2 | N | H | 2,5-(CH₃)₂-C₆H₃ | ethanol | 140–141 | $C_{21}H_{28}O_2N_6$ | 63.61 / 63.46 | 7.12 / 6.96 | 21.20 / 21.13 |

TABLE 8-continued

[Structure: 1,3-dimethylxanthine with 7-position substituent $-(CH_2)_n-N\underset{}{\bigcirc}$ piperidine/piperazine ring bearing R group and X—Z]

| Synthesis Example No. | n | X | R | Z | Recrystallization solvent | Melting point (°C.) | Molecular formula | Elemental analysis (upper value: calculated / lower value: found) |||
|---|---|---|---|---|---|---|---|---|---|---|
| | | | | | | | | C (%) | H (%) | N (%) |
| 27 | 3 | N | H | 2,4-di-CH$_3$-phenyl (CH$_3$, CH$_3$) | ethanol | 128–129 | C$_{22}$H$_{30}$O$_2$N$_6$ | 64.36 / 63.71 | 7.37 / 7.43 | 20.47 / 20.34 |
| 28 | 4 | N | H | 2,4-di-CH$_3$-phenyl | ethanol | 251–252 (decomposed) | C$_{23}$H$_{34}$O$_2$N$_6$·HCl | 59.92 / 59.99 | 7.21 / 7.33 | 18.23 / 18.33 |
| 29 | 5 | N | H | 2,4-di-CH$_3$-phenyl | ethanol/isopropyl ether | 80–83 | C$_{24}$H$_{34}$O$_2$N$_6$·½HCl | 64.39 / 64.63 | 7.90 / 7.92 | 18.78 / 19.26 |
| 30 | 2 | N | H | 2-OCH$_3$-phenyl | methyl cellosolve | 272–273 (decomposed) | C$_{20}$H$_{26}$O$_3$N$_6$·2HCl | 50.95 / 50.76 | 6.00 / 5.68 | 17.83 / 17.52 |
| 31 | 3 | N | H | 2-OCH$_3$-phenyl | methanol | 240–243 (decomposed) | C$_{21}$H$_{28}$O$_3$N$_6$·2HCl | 51.95 / 51.76 | 6.24 / 6.15 | 17.31 / 16.98 |
| 32 | 4 | N | H | 2-OCH$_3$-phenyl | ethanol | 117–118 | C$_{22}$H$_{30}$O$_3$N$_6$ | 61.94 / 62.10 | 7.10 / 7.21 | 19.71 / 19.86 |
| 33 | 5 | N | H | 2-OCH$_3$-phenyl | ethanol | 120–121 | C$_{23}$H$_{32}$O$_3$N$_6$·H$_2$O | 60.23 / 60.50 | 7.49 / 7.20 | 18.33 / 18.37 |
| 34 | 6 | N | H | 2-OCH$_3$-phenyl | ethanol/isopropyl ether | 213–215 (decomposed) | C$_{24}$H$_{34}$O$_3$N$_6$·2HCl | 54.63 / 54.61 | 6.89 / 6.58 | 15.93 / 15.49 |

TABLE 8-continued

[Structure: 1,3-dimethylxanthine with 7-position substituent -(CH₂)ₙ-N(piperazine/piperidine with R)-X-Z]

| Synthesis Example No. | n | X | R | Z | Recrystallization solvent | Melting point (°C.) | Molecular formula | C (%) calc/found | H (%) calc/found | N (%) calc/found |
|---|---|---|---|---|---|---|---|---|---|---|
| 35 | 2 | N | H | 3-OCH₃-phenyl | methyl cellosolve | 170–171 | $C_{20}H_{26}O_3N_6$ | 60.28 / 60.58 | 6.58 / 6.63 | 21.09 / 21.14 |
| 36 | 3 | N | H | 3-OCH₃-phenyl | methyl cellosolve | 161–163 | $C_{21}H_{28}O_3N_6$ | 61.13 / 61.12 | 6.85 / 6.85 | 20.38 / 20.58 |
| 37 | 4 | N | H | 3-OCH₃-phenyl | methanol | 211–212 (decomposed) | $C_{22}H_{30}O_3N_6 \cdot HCl$ | 57.07 / 56.99 | 6.75 / 6.64 | 18.15 / 18.05 |
| 38 | 5 | N | H | 3-OCH₃-phenyl | ethanol | 120–121 | $C_{23}H_{32}O_3N_6 \cdot H_2O$ | 60.23 / 60.50 | 7.49 / 7.20 | 18.33 / 18.37 |
| 39 | 6 | N | H | 3-OCH₃-phenyl | ethanol | 208–210 (decomposed) | $C_{24}H_{34}O_3N_6 \cdot 2HCl$ | 54.64 / 54.51 | 6.88 / 6.91 | 15.93 / 15.99 |
| 40 | 2 | N | H | 4-OCH₃-phenyl | ethanol | 155–156 | $C_{20}H_{26}O_3N_6$ | 60.28 / 60.12 | 6.58 / 6.59 | 21.09 / 21.05 |
| 41 | 3 | N | H | 4-OCH₃-phenyl | methyl cellosolve | 165–167 | $C_{21}H_{28}O_3N_6$ | 61.13 / 61.18 | 6.85 / 6.92 | 20.38 / 20.26 |
| 42 | 4 | N | H | 4-OCH₃-phenyl | ethanol | 115–116 | $C_{22}H_{30}O_3N_6$ | 61.94 / 61.77 | 7.10 / 7.20 | 19.71 / 19.46 |
| 43 | 5 | N | H | 4-OCH₃-phenyl | ethanol | 127–129 | $C_{23}H_{32}O_3N_6$ | 62.69 / 62.36 | 7.33 / 7.33 | 19.08 / 19.41 |

TABLE 8-continued

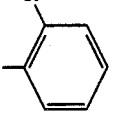

| Synthesis Example No. | n | X | R | Z | Recrystallization solvent | Melting point (°C.) | Molecular formula | C (%) | H (%) | N (%) |
|---|---|---|---|---|---|---|---|---|---|---|
| 44 | 2 | N | H | 2-Cl-C6H4 | ethanol/methyl cellosolve | 161–162 | C19H23O2N6Cl | 56.64 / 56.79 | 5.77 / 5.60 | 20.86 / 20.93 |
| 45 | 3 | N | H | 2-Cl-C6H4 | ethanol | 121–122 | C20H25O2N6Cl | 57.61 / 57.64 | 6.06 / 5.97 | 20.16 / 20.23 |
| 46 | 5 | N | H | 2-Cl-C6H4 | acetone | 117–119 | C22H29O2N6Cl | 59.37 / 59.53 | 6.58 / 6.80 | 18.89 / 19.11 |
| 47 | 2 | N | H | 3-Cl-C6H4 | methyl cellosolve | 134–136 | C19H23O2N6Cl | 56.63 / 56.86 | 5.77 / 5.93 | 20.86 / 20.63 |
| 48 | 3 | N | H | 3-Cl-C6H4 | ethanol | 109–111 | C20H25O2N6Cl | 57.61 / 57.55 | 6.06 / 6.35 | 20.16 / 19.00 |
| 49 | 4 | N | H | 3-Cl-C6H4 | isopropanol/ isopropyl ether | 96–98 | C21H27O2N6Cl | 58.52 / 58.82 | 6.33 / 6.41 | 19.51 / 19.26 |
| 50 | 5 | N | H | 3-Cl-C6H4 | ethanol/ methanol | 151–154 | C22H31O2N6Cl·½H2O | 50.04 / 50.02 | 6.13 / 6.17 | 16.23 / 15.93 |
| 51 | 2 | N | H | 4-Cl-C6H4 | methyl cellosolve | 167–169 | C19H23O2N6Cl | 56.63 / 56.66 | 5.77 / 5.81 | 20.86 / 20.91 |
| 52 | 3 | N | H | 4-Cl-C6H4 | methyl cellosolve | 241–244 (decomposed) | C20H25O2N6Cl·2HCl | 49.03 / 48.66 | 5.57 / 5.20 | 17.16 / 16.84 |

TABLE 8-continued

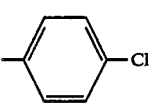

|  |  |  |  |  |  |  |  | Elemental analysis (upper value: calculated / lower value: found) | | |
|---|---|---|---|---|---|---|---|---|---|---|
| Synthesis Example No. | n | X | R | Z | Recrystallization solvent | Melting point (°C.) | Molecular formula | C (%) | H (%) | N (%) |
| 53 | 4 | N | H | 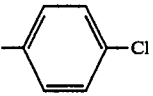 | ethanol | 107–109 | $C_{21}H_{27}O_2N_6Cl$ | 58.52 / 58.77 | 6.33 / 6.38 | 19.50 / 19.44 |
| 54 | 5 | N | H | 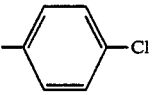 | isopropanol/ ether | 127–130 | $C_{22}H_{29}O_2N_6Cl$ .2HCl | 51.01 / 50.49 | 6.05 / 6.20 | 16.23 / 16.02 |
| 55 | 6 | N | H | 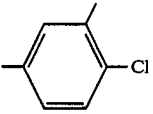 | methanol | 110–111 | $C_{23}H_{31}O_2N_6Cl$ | 60.17 / 60.20 | 6.82 / 6.96 | 18.31 / 18.68 |
| 56 | 2 | N | H | 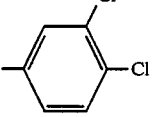 | methyl cellosolve | 146–147 | $C_{19}H_{22}O_2N_6Cl_2$ | 52.18 / 52.23 | 5.07 / 4.95 | 19.22 / 19.39 |
| 57 | 3 | N | H | 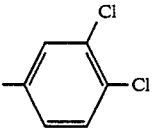 | methyl cellosolve | 124–126 | $C_{20}H_{24}O_2N_6Cl_2$ | 53.21 / 53.50 | 5.37 / 5.32 | 18.62 / 18.52 |
| 58 | 4 | N | H | 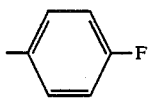 | methanol | 130–132 | $C_{21}H_{26}O_2N_6Cl_2$ | 54.19 / 54.44 | 5.64 / 5.73 | 18.06 / 18.21 |
| 59 | 3 | N | H | 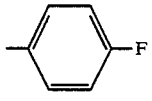 | methanol | 128–129 | $C_{20}H_{25}O_2N_6F$ | 59.97 / 59.94 | 6.30 / 6.31 | 20.99 / 21.12 |
| 60 | 4 | N | H | 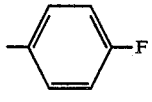 | methanol | 223–226 (decomposed) | $C_{21}H_{27}O_2N_6F$ .2HCl | 51.74 / 51.65 | 6.00 / 5.84 | 17.25 / 16.94 |
| 61 | 5 | N | H | 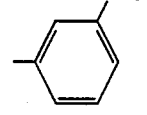 | ethanol/ methanol | 140–141 | $C_{22}H_{29}O_2N_6F$ | 61.65 / 61.32 | 6.83 / 6.77 | 19.61 / 19.67 |
| 62 | 3 | N | H | (3-CF$_3$-phenyl) | methanol | 115–116 | $C_{21}H_{25}O_2N_6F_3$ | 55.98 / 56.46 | 5.60 / 5.71 | 18.66 / 19.26 |

TABLE 8-continued

[Structure: xanthine derivative with N-CH3 groups, (CH2)n-N linked to piperazine/piperidine ring with X-Z and R substituent]

Elemental analysis (upper value: calculated / lower value: found)

| Synthesis Example No. | n | X | R | Z | Recrystallization solvent | Melting point (°C.) | Molecular formula | C (%) | H (%) | N (%) |
|---|---|---|---|---|---|---|---|---|---|---|
| 63 | 4 | N | H | 3-CF3-phenyl | ethanol/isopropyl ether | 215–218 | $C_{22}H_{27}O_2N_6F_3 \cdot 2HCl$ | 49.16 / 49.25 | 5.26 / 5.42 | 15.64 / 16.21 |
| 64 | 5 | N | H | 3-CF3-phenyl | ethanol/isopropyl ether | 114–115 | $C_{23}H_{29}O_2N_6F_3$ | 57.72 / 57.55 | 6.12 / 6.13 | 17.56 / 17.71 |
| 65 | 2 | N | H | 2-pyridyl | methanol | 153–155 | $C_{18}H_{23}O_2N_7$ | 58.51 / 58.48 | 6.29 / 6.38 | 26.54 / 26.22 |
| 66 | 3 | N | H | 2-pyridyl | ethanol | 139–140 | $C_{19}H_{25}O_2N_7$ | 59.50 / 59.52 | 6.58 / 6.65 | 25.57 / 25.80 |
| 67 | 4 | N | H | 2-pyridyl | ethanol | 120–121 | $C_{20}H_{27}O_2N_7$ | 60.42 / 60.14 | 6.06 / 6.90 | 24.67 / 24.40 |
| 68 | 5 | N | H | 2-pyridyl | ethanol/isopropyl ether | 102–104 | $C_{21}H_{20}O_2N_7$ | 61.28 / 61.26 | 7.12 / 7.11 | 23.83 / 23.66 |
| 69 | 6 | N | H | 2-pyridyl | ethanol | 96–97 | $C_{22}H_{31}O_2N_7$ | 62.08 / 62.01 | 7.36 / 7.46 | 23.04 / 23.35 |
| 70 | 3 | N | H | —CH(phenyl)2 | methyl cellosolve | 252–254 | $C_{27}H_{32}O_2N_6 \cdot 2HCl$ | 59.44 / 59.28 | 6.29 / 6.42 | 15.41 / 15.59 |

TABLE 8-continued

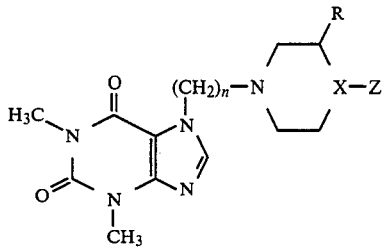

| Synthesis Example No. | n | X | R | Z | Recrystallization solvent | Melting point (°C.) | Molecular formula | Elemental analysis (upper value: calculated / lower value: found) | | |
|---|---|---|---|---|---|---|---|---|---|---|
| | | | | | | | | C (%) | H (%) | N (%) |
| 71 | 4 | N | H | −CH(C$_6$H$_5$)$_2$ | ethanol/methanol | 238–240 | C$_{28}$H$_{34}$O$_2$N$_6$ .2HCl | 60.09 59.14 | 6.50 6.48 | 15.02 14.93 |
| 72 | 5 | N | H | −CH(C$_6$H$_5$)$_2$ | methyl cellosolve | 115–117 (decomposed) | C$_{29}$H$_{36}$O$_2$N$_6$ | 69.56 69.87 | 7.26 7.39 | 16.79 16.70 |
| 73 | 6 | N | H | −CH(C$_6$H$_5$)$_2$ | ethanol | 212–214 | C$_{30}$H$_{38}$O$_2$N$_6$ .2HCl | 61.30 61.27 | 6.87 7.04 | 14.30 14.51 |
| 74 | 2 | N | H | −CH(C$_6$H$_5$)(C$_6$H$_4$Cl) | methyl cellosolve | 250–252 | C$_{26}$H$_{29}$O$_2$N$_6$Cl .2HCl | 55.16 55.19 | 5.53 5.38 | 14.85 14.87 |
| 75 | 3 | N | H | −CH(C$_6$H$_5$)(C$_6$H$_4$Cl) | methyl cellosolve | 222 (decomposed) | C$_{27}$H$_{31}$O$_2$N$_6$Cl .2HCl.H$_2$O | 54.22 53.64 | 5.91 5.92 | 14.06 14.09 |

TABLE 8-continued

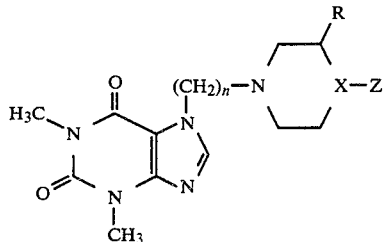

| Synthesis Example No. | n | X | R | Z | Recrystallization solvent | Melting point (°C.) | Molecular formula | Elemental analysis (upper value: calculated / lower value: found) | | |
|---|---|---|---|---|---|---|---|---|---|---|
| | | | | | | | | C (%) | H (%) | N (%) |
| 76 | 4 | N | H | 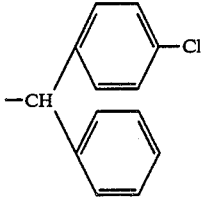 | methanol | 208–210 | $C_{28}H_{33}O_2N_6Cl$ .2HCl | 56.61 56.97 | 5.95 6.04 | 14.15 13.92 |
| 77 | 5 | N | H | 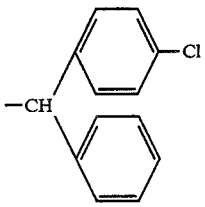 | ethanol/isopropyl ether | 117–119 | $C_{29}H_{35}O_2N_6Cl$ | 65.08 65.23 | 6.60 6.64 | 15.70 16.02 |
| 78 | 6 | N | H | 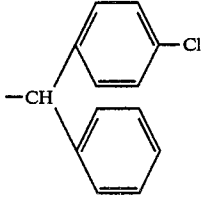 | ethanol | 201–203 | $C_{30}H_{37}O_2N_6Cl$ .2HCl.½H$_2$O | 57.09 57.00 | 6.40 6.54 | 13.32 13.90 |
| 79 | 2 | N | —CH$_3$ | 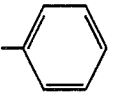 | ethanol | 128–130 | $C_{20}H_{26}O_2N_6$ | 62.80 62.73 | 6.85 6.87 | 21.98 21.91 |
| 80 | 4 | N | —CH$_3$ | 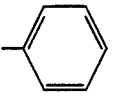 | isopropanol | 99–100 | $C_{22}H_{30}O_2N_6$ | 64.36 64.51 | 7.37 7.47 | 20.47 20.87 |
| 81 | | N | —CH$_3$ | 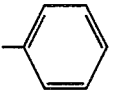 | acetone/isopropyl ether | 111–113 | $C_{21}H_{28}O_2N_6$ | 63.28 63.74 | 7.09 7.12 | 21.09 21.35 |
| 82 | 2 | N | —CH$_3$ | 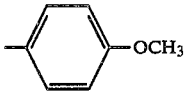 | ethanol | 117–118 | $C_{21}H_{29}N_6O_3$ | 61.14 61.00 | 6.84 6.94 | 20.38 20.23 |
| 83 | 5 | N | —CH$_3$ | 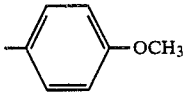 | isopropanol | 85–87 | $C_{24}H_{35}O_3N_6$ | 63.82 63.56 | 6.93 7.69 | 18.61 18.63 |

TABLE 8-continued

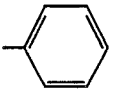

| Synthesis Example No. | n | X | R | Z | Recrystallization solvent | Melting point (°C.) | Molecular formula | C (%) | H (%) | N (%) |
|---|---|---|---|---|---|---|---|---|---|---|
| 84 | 2 | C | H | phenyl | methanol | 155–156 | $C_{20}H_{25}O_2N_5$ | 65.36 / 65.69 | 6.87 / 6.00 | 19.06 / 19.17 |
| 85 | 3 | C | H | phenyl | methyl cellosolve | 157–159 | $C_{21}H_{27}O_2N_5$ | 66.10 / 66.05 | 7.15 / 7.16 | 18.36 / 18.55 |
| 86 | 4 | C | H | phenyl | ethanol | 117–118 | $C_{22}H_{29}O_2N_5$ | 66.80 / 67.01 | 7.40 / 7.51 | 17.71 / 17.70 |
| 87 | 7 | N | —$CH_3$ | 3-Cl-phenyl | ethanol/isopropyl ether | 200–204 | $C_{25}H_{35}O_2N_6$ Cl.HCl.$H_2O$ | 55.44 / 55.36 | 7.09 / 6.88 | 15.52 / 15.92 |
| 88 | 7 | N | H | 2,5-di-$CH_3$-phenyl | hydrous methanol | 239–241 | $C_{26}H_{38}O_2N_6$ .2HCl.½$H_2O$ | 57.02 / 57.46 | 7.38 / 7.45 | 15.35 / 15.77 |
| 89 | 8 | N | H | 2,5-di-$CH_3$-phenyl | hydrous ethanol | 181–183 | $C_{27}H_{40}N_6O_2$ .2HCl | 58.79 / 58.71 | 7.68 / 7.58 | 15.24 / 15.22 |
| 90 | 5 | N | H | 2,3-di-Cl-phenyl | ethanol/isopropyl ether | 112–114 | $C_{22}H_{28}O_2N_6$ .2HCl | 55.11 / 55.09 | 5.90 / 5.93 | 17.53 / 17.31 |
| 91 | 7 | N | H | 2-$CH_3$-4-Cl-phenyl | hydrous methanol | 223–226 (decomposed) | $C_{25}H_{35}O_2N_6Cl$ .2HCl | 53.90 / 53.49 | 6.17 / 6.60 | 15.09 / 15.50 |
| 92 | 10 | N | H | 2-$OCH_3$-phenyl | ethanol | 207–209 (decomposed) | $C_{28}H_{42}O_3N_6$ .2HCl | 57.71 / 57.76 | 7.45 / 7.91 | 14.43 / 14.11 |

TABLE 8-continued

[Structure: theobromine derivative with (CH₂)ₙ-N-piperazinyl-X-Z substituent, R group]

| Synthesis Example No. | n | X | R | Z | Recrystallization solvent | Melting point (°C.) | Molecular formula | C (%) | H (%) | N (%) |
|---|---|---|---|---|---|---|---|---|---|---|
| 93 | 10 | N | H | 4-Cl-C₆H₄-CH₃ | ethanol | 211–213 (decomposed) | $C_{28}H_{41}O_2N_6Cl$ .HCl | 59.45 / 59.31 | 7.50 / 7.50 | 14.80 / 14.69 |
| 94 | 10 | N | —CH₃ | 3-CH₃-C₆H₄ | methanol/isopropyl ether | 211–214 (decomposed) | $C_{29}H_{44}O_2N_6$ .2HCl.2H₂O | 56.38 / 56.12 | 8.17 / 7.76 | 13.60 / 13.46 |
| 95 | 10 | N | H | 2,3-(CH₃)₂-C₆H₃ | methanol/isopropyl ether | 187–190 (decomposed) | $C_{29}H_{44}O_2N_6$ .2HCl | 59.87 / 59.42 | 7.99 / 7.96 | 14.45 / 14.09 |

(upper value: calculated / lower value: found)

SYNTHESIS EXAMPLE 96

1-(4-(4-(2,3-Dimethylphenyl)piperazinyl-(1))-n-butyl)theobromine 9.5 g of 1-(4-bromo-n-butyl)theobromine, 3.8 g of N-(2,3-dimethylphenyl)piperazine and 4.0 g of triethylamine were stirred in toluene under reflux for 13 hours. The triethylamine hydrochloride formed was then filtered off and the filtrate was extracted with dilute hydrochloric acid. The extract was then made alkaline with dilute sodium hydroxide and extracted with chloroform. The chloroform layer was then washed with water and dried over anhydrous calcium carbonate. The solvent was distilled off and the resulting crude crystals were recrystallized from methyl cellosolve to yield 3.7 g of the product compound 1-(4-(4-(2,3-dimethylphenyl)piperazinyl-(1))-n-butyl)theobromine (yield: 43.64%).

Melting point: 134°–135° C.

| Elemental analysis for $C_{23}H_{32}O_2N_6$: | | | |
|---|---|---|---|
| | C | H | N |
| Calculated (%): | 65.05 | 7.61 | 19.80 |
| Found (%): | 65.11 | 7.72 | 19.46 |

SYNTHESIS EXAMPLE 97

1-(5-(4-Benzhydrylpiperazinyl-(1))-n-pentyl)theobromine hydrochloride 7.9 g of 1-(5-bromo-n-pentyl)theobromine, 5.0 g of N-benzylhydrylpiperazine and 4 g of triethylamine were stirred in toluene under reflux for 30 hours, and the mixture was then subjected to the same treatment as in Synthesis Example 96. The resulting crude crystals were converted into a hydrochloride by a known method and the latter was recrystallized from isopropyl alcohol to obtain 4.9 g of the desired compound 1-(5-(4-benzhydrylpiperazinyl-(1))-n-pentyl)theobromine hydrochloride (yield: 40.9%).

Melting point: 262°–264° C. (decomposed)

| Elemental analysis for $C_{29}H_{36}O_2N_6$.2HCl: | | | |
|---|---|---|---|
| | C | H | N |
| Calculated (%): | 60.93 | 6.71 | 14.71 |
| Found (%): | 60.57 | 7.15 | 14.65 |

SYNTHESIS EXAMPLE 98

1-(7-(4-o-Methoxyphenylpiperazinyl-(1))-n-heptyl)-theobromine 7.5 g of 1-(7-bromo-n-heptyl)theobromine, 3.8 g of N-o-methoxyphenylpiperazine and 4.0 g of triethylamine were stirred in toluene under reflux for 11.5 hours, and treated in the same manner as in Synthesis Example 96 to obtain crude crystals. The crystals were purified by silica gel chromatography to obtain 4.6 g of the product compound 1-(7-(4-o-methoxyphenylpiperazinyl-(1))-n-heptyl)theobromine (yield: 49.1%).

Melting point: 97°–98° C.

| Elemental analysis for $C_{25}H_{36}O_3N_6$: | | | |
|---|---|---|---|
| | C | H | N |
| Calculated (%): | 64.08 | 7.74 | 17.94 |
| Found (%): | 60.46 | 6.43 | 21.15 |

SYNTHESIS EXAMPLE 99

1-(2-(4-p-Methoxyphenylpiperazinyl-(1))ethyl)theobromine 6.9 g of 1-(2-bromoethyl)theobromine, 3.8 g of N-p-methoxyphenylpiperazine and 4.0 g of triethylamine were stirred in benzene under reflux. The triethylamine hydrochloride formed was filtered off and the filtrate was then extracted with dilute hydrochloric acid. The resulting extract was made alkaline with dilute sodium hydroxide and further extracted with chloroform. The resulting chloroform layer was washed with water and dried over anhydrous calcium carbonate. The solvent was then distilled off and the resulting crude crystals were recrystallized from methanol to obtain 4.9 g of the product substance 1-(2-(4-p-methoxyphenylpiperazinyl-(1))-ethyl)theobromine (yield: 61.3%).

Melting point: 157°–159° C.

| Elemental analysis for $C_{20}H_{26}O_3N_6$: | | | |
|---|---|---|---|
| | C | H | N |
| Calculated (%): | 60.27 | 6.59 | 21.09 |
| Found (%): | 60.46 | 6.43 | 21.15 |

SYNTHESIS EXAMPLE 100

1-(3-(4-o-Methylphenylpiperazinyl-(1))-n-propyl)theobromine 7.2 g of 1-(3-bromo-n-propyl)theobromine, 3.5 g of N-o-methylphenylpiperazine and 4.0 g of triethylamine were stirred in a benzene solvent under reflux for 16 hours and the mixture was treated in the same way as in Synthesis Example 99. The resulting crude crystals were recrystallized from ethanol to obtain 6.3 g of the objective compound 1-(3-(4-o-methylphenylpiperazinyl-(1))-n-propyl)theobromine (yield: 91.3%).

Melting point: 152°–154° C.

| Elemental analysis for $C_{21}H_{28}O_2N_6$: | | | |
|---|---|---|---|
| | C | H | N |
| Calculated (%): | 63.60 | 7.13 | 21.20 |
| Found (%): | 63.40 | 7.20 | 21.31 |

SYNTHESIS EXAMPLE 101

1-(4-(4-p-Chlorobenzylhomopiperazinyl-(1))-n-butyl)-theobromine 7.5 g of 1-(4-bromo-n-butyl)theobromine, 4.5 g of N-p-chlorobenzylhomopiperazine and 4.0 g of triethylamine were stirred in a benzene solvent under reflux and then treated in the same manner as in Synthesis Example 4. To the obtained oily substance was added isopropyl ether and left under ice cooling to have it crystallized. The formed crude crystals were recrystallized from ethanol to obtain 5.8 g of 1-(4-(4-p-chlorobenzylhomopiperazinyl-(1))-n-butyl)theobromine (yield: 67.5%).

Melting point: 71°–73° C.

| Elemental analysis for $C_{23}H_{31}O_2N_6Cl$: | | | |
|---|---|---|---|
| | C | H | N |
| Calculated (%): | 60.17 | 6.82 | 18.31 |
| Found (%): | 59.94 | 6.86 | 18.43 |

SYNTHESIS EXAMPLE 102

1-(5-(4-piperidoneethyleneketal)yl-(1))-n-pentyl)theobromine 7.9 g of 1-(5-bromo-n-pentyl)theobromine, 3.5 g of 4-piperidone ethylene ketal and 4.0 g of triethylamine were stirred in a benzene solvent under reflux and the reaction mixture was washed with water and dried over anhydrous potassium carbonate. The solvent was distilled off and the resulting crude crystals were recrystallized from acetone/isopropyl to obtain 5.3 g of the objective compound 1-(5-(4-(piperidoneethyleneketal)yl-(1))-n-pentyl)theobromine (yield: 69.0%).

Melting point: 95°–96° C.

| Elemental analysis for $C_{19}H_{29}O_4N_5$: | | | |
|---|---|---|---|
| | C | H | N |
| Calculated (%): | 58.29 | 7.48 | 17.88 |
| Found (%): | 58.06 | 7.54 | 18.02 |

SYNTHESIS EXAMPLES 103 TO 193

The compounds shown in Table 9 were obtained using procedures similar to the procedures used in Synthesis Example 96.

TABLE 9

| Synthesis Example No. | n | R | Z | Melting point (°C.) | Molecular formula | Elemental analysis (upper value: calculated / lower value: found) C (%) | H (%) | N (%) |
|---|---|---|---|---|---|---|---|---|
| 103 | 6 | H | 3-CH₃-C₆H₄ | 197–198 (decomposed) | $C_{24}H_{34}N_6O_2 \cdot 2HCl \cdot 2H_2O$ | 52.65 / 52.64 | 7.01 / 7.10 | 15.35 / 15.28 |
| 104 | 2 | H | 3-CH₃-C₆H₄ | 251 (decomposed) | $C_{20}H_{26}O_2N_6 \cdot 2HCl$ | 52.75 / 52.41 | 6.21 / 6.11 | 18.46 / 18.31 |
| 105 | 5 | H | 3-CH₃-C₆H₄ | 133–135 | $C_{23}H_{32}O_2N_6$ | 65.05 / 65.03 | 7.61 / 7.62 | 19.80 / 19.82 |
| 106 | 6 | H | 3-CH₃-C₆H₄ | 206–208 (decomposed) | $C_{24}H_{34}O_2N_6 \cdot 2HCl \cdot 2H_2O$ | 52.65 / 53.10 | 7.01 / 6.91 | 15.35 / 15.44 |
| 107 | 2 | H | 2,3-(CH₃)₂-C₆H₃ | 151–153 | $C_{21}H_{28}O_2N_6$ | 63.60 / 63.60 | 7.13 / 7.05 | 21.20 / 21.28 |
| 108 | 3 | H | 2,3-(CH₃)₂-C₆H₃ | 154–156 | $C_{22}H_{30}O_2N_6$ | 64.36 / 64.13 | 7.37 / 7.49 | 20.47 / 20.32 |
| 109 | 4 | H | 2,3-(CH₃)₂-C₆H₃ | 124–126 | $C_{23}H_{32}O_2N_6$ | 65.05 / 65.03 | 7.61 / 7.61 | 19.80 / 19.82 |
| 110 | 5 | H | 2,3-(CH₃)₂-C₆H₃ | 121–123 | $C_{24}H_{34}O_2N_6$ | 65.71 / 65.68 | 7.38 / 7.73 | 19.16 / 19.36 |
| 111 | 2 | H | 2,6-(CH₃)₂-C₆H₃ | 161–162 | $C_{21}H_{28}O_2N_6$ | 63.60 / 63.67 | 7.13 / 7.07 | 21.20 / 21.16 |
| 112 | 3 | H | 2,6-(CH₃)₂-C₆H₃ | 124–126 | $C_{22}H_{30}O_2N_6$ | 64.36 / 63.65 | 7.37 / 7.20 | 20.47 / 20.32 |
| 113 | 4 | H | 2,6-(CH₃)₂-C₆H₃ | 134–135 | $C_{23}H_{32}O_2N_6$ | 65.05 / 65.11 | 7.61 / 7.72 | 19.80 / 19.46 |

TABLE 9-continued

[Structure: 1,3-dimethylxanthine derivative with -C(O)-N(CH₂)ₙ-N[piperazine ring with R]-N-Z]

| Synthesis Example No. | n | R | Z | Melting point (°C.) | Molecular formula | C (%) | H (%) | N (%) |
|---|---|---|---|---|---|---|---|---|
| 114 | 5 | H | 2,6-(CH₃)₂-C₆H₃ | 118–120 | C₂₄H₃₄O₂N₆ | 65.71 / 65.65 | 7.38 / 7.95 | 19.16 / 18.94 |
| 115 | 6 | H | 2,6-(CH₃)₂-C₆H₃ | 91–93 | C₂₅H₃₀O₂N₆ | 66.34 / 65.84 | 8.02 / 8.31 | 18.57 / 18.50 |
| 116 | 2 | H | 2,4-(CH₃)₂-C₆H₃ | 139–141 | C₂₁H₂₈O₂N₆ | 63.61 / 63.73 | 7.12 / 7.30 | 21.20 / 21.21 |
| 117 | 3 | H | 2,4-(CH₃)₂-C₆H₃ | 137–139 | C₂₂H₃₀O₂N₆ | 64.36 / 64.19 | 7.37 / 7.44 | 20.47 / 20.36 |
| 118 | 4 | H | 2,4-(CH₃)₂-C₆H₃ | 148–150 | C₂₃H₃₂O₂N₆ | 65.05 / 64.44 | 7.61 / 7.52 | 19.80 / 19.70 |
| 119 | 5 | H | 2,4-(CH₃)₂-C₆H₃ | 99–101 | C₂₄H₃₄O₂N₆ | 65.71 / 65.33 | 7.38 / 7.79 | 19.16 / 19.12 |
| 120 | 6 | H | 2,4-(CH₃)₂-C₆H₃ | 89–90 | C₂₅H₃₆O₂N₆ | 66.33 / 66.26 | 8.03 / 8.21 | 18.57 / 18.24 |
| 121 | 5 | H | 3-OCH₃-C₆H₄ | 165–166 (decomposed) | C₂₃H₃₂O₃N₆·HCl | 57.91 / 57.81 | 6.97 / 7.19 | 17.62 / 17.21 |
| 122 | 6 | H | 3-OCH₃-C₆H₄ | 79–81 | C₂₄H₃₄O₃N₆ | 63.40 / 63.35 | 7.55 / 7.70 | 18.49 / 18.69 |
| 123 | 2 | H | 2-Cl-C₆H₄ | 122–124 | C₁₉H₂₃O₂N₆Cl | 56.63 / 56.67 | 5.77 / 5.67 | 20.86 / 21.19 |
| 124 | 4 | H | 2-Cl-C₆H₄ | 111–113 | C₂₁H₂₇O₂N₆Cl·½H₂O | 57.33 / 57.53 | 6.65 / 6.29 | 19.10 / 19.14 |

TABLE 9-continued

Structure: 1,3-dimethylxanthine-8-carboxamide derivative with formula showing $N-(CH_2)_n-N$ linked to piperazine $N-Z$ with R substituent.

| Synthesis Example No. | n | R | Z | Melting point (°C.) | Molecular formula | C (%) | H (%) | N (%) |
|---|---|---|---|---|---|---|---|---|
| 125 | 6 | H | 3-Cl-phenyl | 106–107 | $C_{23}H_{31}O_2N_6Cl$ | 60.17 / 60.21 | 6.82 / 6.97 | 18.31 / 18.63 |
| 126 | 2 | —CH$_3$ | phenyl | 176–178 | $C_{20}H_{26}O_2N_6$ | 62.79 / 63.19 | 6.87 / 6.89 | 21.98 / 22.03 |
| 127 | 3 | —CH$_3$ | phenyl | 126–128 | $C_{21}H_{28}O_2N_6$ | 63.61 / 63.56 | 7.12 / 7.28 | 21.20 / 21.54 |
| 128 | 4 | —CH$_3$ | phenyl | 120–122 | $C_{22}H_{30}O_2N_6$ | 64.35 / 64.81 | 7.38 / 7.47 | 20.47 / 20.37 |
| 129 | 5 | —CH$_3$ | phenyl | 102–104 | $C_{23}H_{32}O_2N_6$ | 65.07 / 65.10 | 7.60 / 7.77 | 19.80 / 19.82 |
| 130 | 6 | —CH$_3$ | phenyl | 101–103 | $C_{24}H_{34}O_2N_6$ | 65.71 / 65.64 | 7.38 / 7.95 | 19.16 / 19.19 |
| 131 | 2 | —CH$_3$ | 4-OCH$_3$-phenyl | 118–119 | $C_{21}H_{28}O_3N_6 \cdot \frac{1}{2}H_2O$ | 60.27 / 60.73 | 6.28 / 6.81 | 20.09 / 20.15 |
| 132 | 3 | —CH$_3$ | 4-OCH$_3$-phenyl | 142–143 | $C_{22}H_{30}O_3N_6$ | 61.95 / 61.95 | 7.09 / 7.13 | 19.71 / 19.91 |
| 133 | 4 | —CH$_3$ | 4-OCH$_3$-phenyl | 108–110 | $C_{23}H_{32}O_3N_6$ | 62.70 / 62.84 | 7.32 / 7.39 | 19.08 / 19.24 |
| 134 | 3 | H | 3,4-diCl-phenyl | 162–163 | $C_{20}H_{24}O_2N_6Cl_2$ | 53.21 / 53.11 | 5.37 / 5.41 | 18.62 / 18.62 |
| 135 | 4 | H | 3,4-diCl-phenyl | 140–142 | $C_{21}H_{26}O_2N_6Cl_2$ | 54.19 / 54.24 | 5.64 / 5.71 | 18.06 / 17.91 |
| 136 | 5 | H | 3,4-diCl-phenyl | 132–134 | $C_{22}H_{28}O_2N_6Cl_2$ | 55.11 / 55.03 | 5.90 / 5.86 | 17.53 / 17.65 |
| 137 | 6 | H | 3,4-diCl-phenyl | 144–145 | $C_{23}H_{30}O_2N_6Cl_2$ | 55.57 / 56.04 | 6.14 / 6.32 | 17.03 / 17.09 |
| 138 | 2 | H | —CH(phenyl)$_2$ | 175–176 | $C_{26}H_{30}O_2N$ | 68.10 / 68.20 | 6.59 / 6.57 | 18.33 / 18.50 |

TABLE 9-continued

Structure:
1,3-dimethylxanthine-type core with $-C(O)-N(-(CH_2)_n-N\text{-piperazine-}N-Z)$ substituent where piperazine bears R group.

| Synthesis Example No. | n | R | Z | Melting point (°C.) | Molecular formula | C (%) calc/found | H (%) calc/found | N (%) calc/found |
|---|---|---|---|---|---|---|---|---|
| 139 | 3 | H | -CH(C6H5)2 | 150–151 | $C_{27}H_{32}O_2N_6$ | 68.62 / 68.66 | 6.83 / 6.87 | 17.79 / 17.85 |
| 140 | 4 | H | -CH(C6H5)2 | 163–165 | $C_{28}H_{34}O_2N_6$ | 69.10 / 68.96 | 7.06 / 7.00 | 17.27 / 17.22 |
| 141 | 5 | H | -CH(C6H5)2 | 262–264 | $C_{29}H_{36}O_2N_6 \cdot 2HCl$ | 60.93 / 60.57 | 6.71 / 7.15 | 14.71 / 14.65 |
| 142 | 2 | H | -CH(C6H4Cl)(C6H5) | 228–230 (decomposed) | $C_{26}H_{29}O_2N_6Cl \cdot 2HCl \cdot H_2O$ | 53.48 / 54.05 | 5.70 / 5.45 | 14.40 / 14.35 |
| 143 | 3 | H | -CH(C6H4Cl)(C6H5) | 194–195 (decomposed) | $C_{27}H_{31}O_2N_6Cl \cdot 2HCl \cdot 2H_2O$ | 52.64 / 53.21 | 5.74 / 5.95 | 13.64 / 13.74 |
| 144 | 4 | H | -CH(C6H4Cl)(C6H5) | 142–144 | $C_{28}H_{33}O_2N_6Cl$ | 64.53 / 64.76 | 6.40 / 6.52 | 16.13 / 16.16 |
| 145 | 5 | H | -CH(C6H4Cl)(C6H5) | 85–87 | $C_{29}H_{35}O_2N_6Cl \cdot 2HCl$ | 57.47 / 56.96 | 6.17 / 6.68 | 13.87 / 13.73 |
| 146 | 6 | H | -CH(C6H4Cl)(C6H5) | 85–88 | $C_{30}H_{37}O_2N_6Cl \cdot 2HCl$ | 57.92 / 57.56 | 6.33 / 6.69 | 13.51 / 13.14 |
| 147 | 7 | H | -C6H4-F | 81–83 | $C_{24}H_{33}O_2N_6F$ | 63.12 / 62.69 | 7.30 / 7.33 | 18.41 / 18.33 |
| 148 | 7 | H | -C6H4-CH3 | 90–91 | $C_{25}H_{36}O_2N_6$ | 66.34 / 66.24 | 8.02 / 8.03 | 18.57 / 18.54 |

TABLE 9-continued

Structure:

$$\text{7-methyl-xanthine core}-N-(CH_2)_n-N\text{(piperazine with R)}-N-Z$$

(1,3-dimethylxanthine with N—(CH₂)ₙ—N[piperazinyl with R substituent]—N—Z)

| Synthesis Example No. | n | R | Z | Melting point (°C.) | Molecular formula | C (%) | H (%) | N (%) |
|---|---|---|---|---|---|---|---|---|
| 149 | 3 | H | 2-Cl-phenyl | 252–253 (decomposed) | $C_{20}H_{25}N_6O_2Cl \cdot HCl \cdot \frac{1}{2}H_2O$ | 51.96 / 51.98 | 5.89 / 6.11 | 18.18 / 18.17 |
| 150 | 8 | H | 2-OCH₃-phenyl | 173–177 | $C_{26}H_{38}N_6O_3 \cdot 2HCl \cdot H_2O$ | 54.44 / 54.19 | 7.38 / 7.37 | 14.65 / 14.67 |
| 151 | 8 | H | 2,6-(CH₃)₂-phenyl | 228–230 | $C_{27}H_{40}N_6O_2 \cdot HCl$ | 62.95 / 62.91 | 8.62 / 8.04 | 16.32 / 16.41 |
| 152 | 10 | H | 2,4-(CH₃)₂-phenyl | 147–150 | $C_{29}H_{44}N_6O_2 \cdot 2HCl \cdot H_2O$ | 58.08 / 58.28 | 8.07 / 8.08 | 14.02 / 13.94 |
| 153 | 10 | —CH₃ | 3-OCH₃-phenyl | 154–157 | $C_{29}H_{44}N_6O_3 \cdot 2HCl \cdot \frac{1}{2}H_2O$ | 57.44 / 57.32 | 7.81 / 7.92 | 13.86 / 13.84 |
| 154 | 4 | H | 2-OCH₃-phenyl | 221–222 (decomposed) | $C_{22}H_{30}N_6O_3 \cdot 2HCl \cdot H_2O$ | 51.06 / 50.93 | 6.43 / 6.53 | 16.24 / 16.23 |
| 155 | 4 | H | 2,3-Cl₂-phenyl | 205–206 (decomposed) | $C_{21}H_{26}N_6O_2Cl_2 \cdot HCl \cdot H_2O$ | 48.51 / 48.25 | 5.62 / 5.62 | 16.17 / 16.22 |
| 156 | 2 | H | 2-OCH₃-phenyl | 164–166 | $C_{20}H_{26}O_3N_6$ | 60.27 / 60.45 | 6.59 / 6.53 | 21.09 / 20.97 |
| 157 | 2 | H | 3-OCH₃-phenyl | 145–146 | $C_{20}H_{26}O_3N_6$ | 60.27 / 60.33 | 6.59 / 6.66 | 21.09 / 21.10 |
| 158 | 2 | H | 2-CH₃-phenyl | 115–117 | $C_{20}H_{26}O_2N_6$ | 62.79 / 62.63 | 6.87 / 7.04 | 21.98 / 21.83 |
| 159 | 2 | H | 4-Cl-phenyl | 199–200 | $C_{19}H_{23}O_2N_6Cl$ | 56.63 / 56.61 | 5.77 / 5.79 | 20.86 / 20.83 |
| 160 | 2 | H | 3-Cl-phenyl | 171–172 | $C_{19}H_{25}O_2N_6Cl$ | 56.63 / 56.80 | 5.77 / 5.61 | 20.86 / 20.90 |
| 161 | 2 | H | 4-F-phenyl | 183–185 | $C_{19}H_{23}O_2N_6F$ | 59.04 / 58.93 | 6.01 / 5.97 | 21.75 / 21.67 |

TABLE 9-continued

| Synthesis Example No. | n | R | Z | Melting point (°C.) | Molecular formula | Elemental analysis (upper value: calculated / lower value: found) | | |
|---|---|---|---|---|---|---|---|---|
| | | | | | | C (%) | H (%) | N (%) |
| 162 | 2 | H |  (CF3) | 156–158 | $C_{20}H_{23}O_2N_6F_3 \cdot \frac{1}{2}H_2O$ | 53.92 / 53.57 | 5.21 / 5.26 | 18.87 / 19.03 |
| 163 | 3 | H |  | 142–144 | $C_{20}H_{26}O_2N_6$ | 62.79 / 62.86 | 6.87 / 6.93 | 21.98 / 22.17 |
| 164 | 3 | H |  (OCH3, ortho) | 180–182 | $C_{21}H_{28}O_3N_6$ | 61.13 / 61.05 | 6.85 / 6.72 | 20.38 / 20.41 |
| 165 | 3 | H |  (OCH3, meta) | 94–96 | $C_{21}H_{28}O_3N_6$ | 61.13 / 61.00 | 6.85 / 6.93 | 20.38 / 20.35 |
| 166 | 3 | H |  (OCH3, para) | 164–167 | $C_{21}H_{28}O_3N_6$ | 61.13 / 61.35 | 6.85 / 6.67 | 20.38 / 20.67 |
| 167 | 3 | H |  (Cl) | 151–152 | $C_{20}H_{25}O_2N_6Cl$ | 57.60 / 57.84 | 6.05 / 6.17 | 20.16 / 20.25 |
| 168 | 3 | H |  (Cl, para) | 165–167 | $C_{20}H_{25}O_2N_6Cl$ | 57.58 / 57.63 | 6.06 / 6.08 | 20.17 / 20.21 |
| 169 | 3 | H |  (F) | 160–161 | $C_{20}H_{25}O_2N_6F$ | 59.95 / 59.90 | 6.31 / 6.27 | 20.99 / 21.17 |
| 170 | 3 | H |  (CF3) | 116–118 | $C_{21}H_{25}O_2N_6F_3$ | 55.98 / 55.88 | 5.60 / 5.63 | 18.66 / 18.68 |
| 171 | 4 | H |  | 156–158 | $C_{21}H_{28}O_2N_6$ | 63.60 / 63.68 | 7.13 / 7.12 | 21.20 / 21.10 |
| 172 | 4 | H |  (OCH3, ortho) | 126–127 | $C_{22}H_{30}O_3N_6$ | 61.94 / 62.10 | 7.10 / 7.08 | 19.70 / 19.50 |
| 173 | 4 | H |  (OCH3, meta) | 69–73 | $C_{22}H_{30}O_3N_6$ | 61.94 / 61.98 | 7.10 / 7.00 | 19.70 / 19.63 |
| 174 | 4 | H |  (OCH3, para) | 145–146 | $C_{22}H_{30}O_3N_6$ | 61.94 / 62.11 | 7.10 / 6.95 | 19.70 / 19.76 |
| 175 | 4 | H | (CH3) | 132–134 | $C_{22}H_{30}O_2N_6$ | 64.35 / 64.80 | 7.38 / 7.52 | 20.47 / 20.79 |

TABLE 9-continued

[Structure: 1,3-dimethylxanthine with N-(CH2)n-N-piperazine-N-Z substituent, R on piperazine]

| Synthesis Example No. | n | R | Z | Melting point (°C.) | Molecular formula | Elemental analysis (upper value: calculated / lower value: found) | | |
|---|---|---|---|---|---|---|---|---|
| | | | | | | C (%) | H (%) | N (%) |
| 176 | 4 | H | 3-Cl-phenyl | 125 | $C_{21}H_{27}O_2N_6Cl$ | 58.52 / 58.54 | 6.33 / 6.31 | 19.53 / 19.51 |
| 177 | 4 | H | 4-Cl-phenyl | 170–171 | $C_{21}H_{27}O_2N_6Cl$ | 58.52 / 58.67 | 6.33 / 6.23 | 19.53 / 19.55 |
| 178 | 4 | H | 4-F-phenyl | 129–131 | $C_{21}H_{27}O_2N_6F$ | 60.84 / 60.82 | 6.58 / 6.52 | 20.28 / 20.19 |
| 179 | 4 | H | 3-CF3-phenyl | 120–122 | $C_{22}H_{27}O_2N_6F_3$ | 56.88 / 56.84 | 5.87 / 5.84 | 18.09 / 18.01 |
| 180 | 5 | H | phenyl | 113–115 | $C_{22}H_{30}O_2N_6$ | 64.36 / 64.20 | 7.37 / 7.41 | 20.47 / 20.58 |
| 181 | 5 | H | 2-CH3-phenyl | 98–99 | $C_{23}H_{32}O_2N_6$ | 65.05 / 64.92 | 7.61 / 7.56 | 19.80 / 19.69 |
| 182 | 5 | H | 2-OCH3-phenyl | 135–137 | $C_{23}H_{32}O_3N_6$ | 62.69 / 62.53 | 7.34 / 7.43 | 19.08 / 19.07 |
| 183 | 5 | H | 2-methyl-4-OCH3-phenyl | 120–121 | $C_{23}H_{32}O_3N_6$ | 62.69 / 62.89 | 7.33 / 7.38 | 19.08 / 18.95 |
| 184 | 5 | H | 3-Cl-phenyl | 163–164 | $C_{22}H_{29}O_2N_6Cl$ | 59.37 / 59.55 | 6.58 / 6.57 | 18.89 / 18.73 |
| 185 | 5 | H | 4-Cl-phenyl | 168–170 | $C_{22}H_{29}O_2N_6Cl$ | 59.37 / 59.48 | 6.58 / 6.52 | 18.89 / 18.85 |
| 186 | 5 | H | 4-F-phenyl | 130–132 | $C_{22}H_{29}O_2N_6F$ | 61.65 / 61.56 | 6.83 / 6.79 | 19.61 / 19.73 |
| 187 | 5 | H | 3-CF3-phenyl | 133–135 | $C_{23}H_{29}O_2N_6F_3$ | 57.72 / 57.63 | 6.12 / 6.16 | 17.56 / 17.53 |
| 188 | 6 | H | phenyl | 106–107 | $C_{23}H_{32}O_2N_6$ | 65.05 / 65.11 | 7.61 / 7.52 | 19.80 / 19.58 |
| 189 | 6 | H | 2-OCH3-phenyl | 108–109 | $C_{24}H_{34}O_3N_6$ | 63.40 / 63.14 | 7.55 / 7.34 | 18.49 / 18.37 |

TABLE 9-continued $$\text{structure with } CH_3\text{-N-imidazole, C=O, N-(CH}_2)_n\text{-N-piperazine-N-Z, and N-CH}_3$$

| Synthesis Example No. | n | R | Z | Melting point (°C.) | Molecular formula | Elemental analysis (upper: calculated, lower: found) C (%) | H (%) | N (%) |
|---|---|---|---|---|---|---|---|---|
| 190 | 6 | H | -C₆H₄-OCH₃ | 105–107 | $C_{24}H_{34}O_3N_6$ | 63.40 / 62.98 | 7.55 / 7.23 | 18.49 / 18.16 |
| 191 | 6 | H | -C₆H₄-Cl | 159–160 | $C_{23}H_{31}O_2N_6Cl$ | 60.17 / 60.34 | 6.82 / 6.90 | 18.31 / 18.46 |
| 192 | 6 | H | -C₆H₄-F | 135–136 | $C_{23}H_{31}O_2N_6F$ | 62.41 / 62.46 | 7.07 / 7.05 | 18.99 / 18.95 |
| 193 | 6 | H | -C₆H₄-CF₃ | 110–111 | $C_{24}H_{31}O_2N_6F_3$ | 58.51 / 58.45 | 6.36 / 6.32 | 17.06 / 17.10 |

Some typical examples of pharmaceutical preparations used in the present invention are given below.

EXAMPLE 1: Tablet

| | |
|---|---|
| 7-(3-(4-(3,4-Dimethyl)phenyl-piperazinyl-(1))-n-propyl)-theophylline.2HCl | 10.0 parts |
| Lactose | 53.5 parts |
| Crystallite cellulose | 18.0 parts |
| Corn starch | 18.0 parts |
| Calcium stearate | 0.5 parts |

The above materials were mixed, granulated and compression molded according to a conventional method to obtain tablets weighing 100 mg each.

EXAMPLE 2: Capsule

| | |
|---|---|
| 7-(5-(4-m-trifluoromethyl-phenylpiperazinyl-(1))-n-pentyl)theophylline.2HCl | 10.0 parts |
| Lactose | 70.0 parts |
| Corn starch | 20.0 parts |

The above materials were processed according to the conventional method to prepare capsules weighing 100 mg each.

EXAMPLE 3: Tablet

| | |
|---|---|
| 1-(3-(4-(3,4-Dichloro)phenyl-piperazinyl-(1))-n-propyl)-theobromine | 10.0 parts |
| Lactose | 53.5 parts |
| Crystallite cellulose | 18.0 parts |
| Corn starch | 18.0 parts |
| Calcium stearate | 0.5 parts |

The above materials were mixed, granulated and then compression molded to obtain tablets each weighing 100 mg each according to a conventional method.

EXAMPLE 4: Capsule

| | |
|---|---|
| 1-(5-(4-m-Methylphenyl-piperazinyl-(1))-n-pentyl)theobromine | 10.0 parts |
| Lactose | 70.0 parts |
| Corn starch | 20.0 parts |

The above materials were processed according to the conventional method to prepare capsules weighing 100 mg each.

The embodiments of the invention in which an exclusive property or privilege is claimed are defined as follows:

1. A method for treating a subject suffering from at least one of the symptoms of pain, fever, and tissue and/or bone and joint inflammation, which comprises administering to the subject a pharmaceutical composition which comprises a therapeutically effective amount of at least one compound of the general formula:

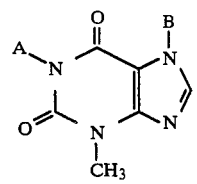

wherein one of A and B is —CH₃ and the other of A and B is

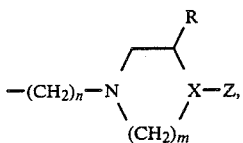

wherein R is a hydrogen atom or a lower alkyl group, Z is selected from the group consisting of (1) a group of the formula

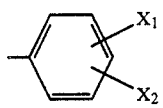

wherein $X_1$ and $X_2$ are the same or different and each represents a hydrogen atom, a lower alkyl group, a lower alkoxy group, a trifluoromethyl group or a halogen atom; (2) a pyridyl group; and (3) a group of the formula:

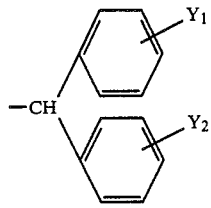

wherein $Y_1$ and $Y_2$ are the same or different and $Y_1$ and $Y_2$ are selected from the group consisting of a hydrogen atom, a lower alkyl group, a lower alkoxy group, a trifluoromethyl group and a halogen atom, X is a nitrogen atom or a carbon atom, m is 2 or 3, and n is an integer of from 2 to 10, with the provisos that (i) when A is —CH₃, m is 2, (ii) when A is

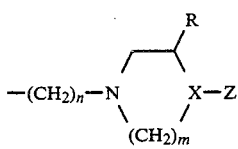

Z is not pyridyl and X is nitrogen and (iii) when X is nitrogen, m is 3, and acid addition salts thereof, for analgesic, antiphlogistic, and antipyretic purposes, in combination with a pharmaceutically effective carrier.

2. A method as claimed in claim 1 in which said subject suffers from pain.

3. A method as claimed in claim 1 in which said subject suffers from fever.

4. A method as claimed in claim 1 in which said subject suffers from tissue and/or bone and joint inflammation.

5. A method as claimed in claim 3, wherein said compound has the formula

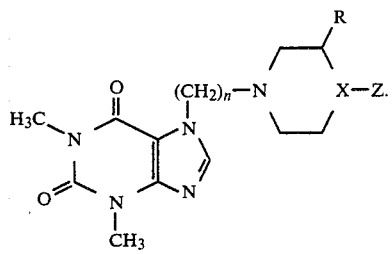

6. A method as claimed in claim 4, wherein said compound has the formula

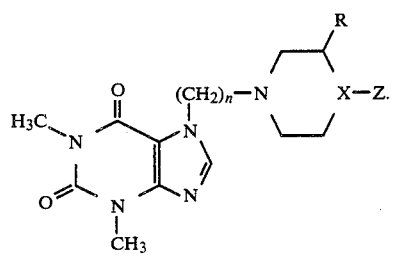

7. A method as claimed in claim 1, wherein said compound is administered to said subject in a dosage of from 1 to 1,000 mg per day.

8. A method as claimed in claim 2, wherein said compound is administered to said subject in a dosage of 1 to 1,000 mg per day.

9. A method as claimed in claim 3, wherein said compound is administered to said subject in a dosage of 1 to 1,000 mg per day.

10. A method as claimed in claim 4, wherein said compound is administered to said subject in a dosage of 1 to 1,000 mg per day.

11. A method according to claim 1 wherein said compound is selected from the group consisting of
7-(2-((4-phenyl)piperidinyl)ethyl)theophylline,
7-(3-((4-phenyl)piperidinyl)-n-propyl)theophylline,
7-(4-((4-phenyl)piperidinyl)-n-butyl)theophylline, and
7-(5-((4-p-chlorophenyl)piperidinyl)-n-pentyl)theophylline.

12. A method according to claim 1 wherein said compound is
1-(4-(4-p-chlorobenzylhomopiperazinyl-(1)-n-butyl)-theobromine.

* * * * *

UNITED STATES PATENT AND TRADEMARK OFFICE
CERTIFICATE OF CORRECTION

PATENT NO. : 4 599 337
DATED : July 8, 1986
INVENTOR(S) : Takeru KANEKO et al

It is certified that error appears in the above-identified patent and that said Letters Patent is hereby corrected as shown below:

Column 60, line 58; add the following claim:

---13. A method as claimed in Claim 2, wherein said compound has the formula

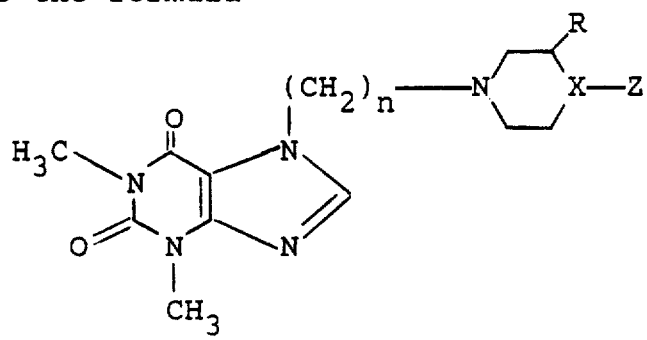

On the Title Page, "12 Claims" should read -- 13 Claims --.

Signed and Sealed this

Twenty-fourth Day of March, 1987

Attest:

DONALD J. QUIGG

Attesting Officer     Commissioner of Patents and Trademarks